(12) United States Patent
Strom et al.

(10) Patent No.: US 7,579,439 B2
(45) Date of Patent: Aug. 25, 2009

(54) MODULATION OF IL-2- AND IL-15-MEDIATED T CELL RESPONSES

(75) Inventors: Terry B. Strom, Brookline, MA (US); Xian Chang Li, Newton, MA (US); Xin Xiao Zheng, Pittsburgh, PA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 120 days.

(21) Appl. No.: 10/749,699

(22) Filed: Dec. 30, 2003

(65) Prior Publication Data

US 2004/0185048 A1    Sep. 23, 2004

Related U.S. Application Data

(63) Continuation of application No. 10/749,699, filed on Dec. 30, 2003, which is a continuation of application No. 09/953,323, filed on Sep. 14, 2001, now abandoned.

(60) Provisional application No. 60/232,251, filed on Sep. 14, 2000.

(51) Int. Cl.
C07K 14/55 (2006.01)
A61K 45/00 (2006.01)
A61K 39/385 (2006.01)
C07K 14/47 (2006.01)

(52) U.S. Cl. .................. 530/351; 424/85.2; 424/192.1; 514/12

(58) Field of Classification Search .................. None
See application file for complete search history.

(56) References Cited

U.S. PATENT DOCUMENTS

| | | | |
|---|---|---|---|
| 5,011,684 A | 4/1991 | Strom | |
| 5,116,964 A | 5/1992 | Capon et al. | |
| 5,552,303 A | 9/1996 | Grabstein et al. | |
| 5,574,138 A | 11/1996 | Grabstein et al. | |
| 5,707,616 A | 1/1998 | Grabstein et al. | |
| 5,747,024 A | 5/1998 | Grabstein et al. | |
| 5,892,001 A | 4/1999 | Grabstein et al. | |

FOREIGN PATENT DOCUMENTS

| | | |
|---|---|---|
| DE | 198 23 351 A1 | 5/1998 |
| WO | WO 88/07089 | 9/1988 |
| WO | WO 92/12726 | 8/1992 |
| WO | WO 94/06473 | 3/1994 |
| WO | WO 96/26274 | 8/1996 |
| WO | WO 97/41232 | 11/1997 |
| WO | WO 98/36768 | 8/1998 |

OTHER PUBLICATIONS

Kim et al. The Journal of Immunlogy, 1998. vol. 160, pp. 5742-5748.*
Strom et al. Transplantaion Proceedings, 1995, vol. 27, No. 5, Suppl 1, pp. 18-20.*
Bernard et al, The Journal of Biological Chemistry, Jun. 2004, vol. 279, No. 23, pp. 24313-24322.*
Wells, Biochemistry, 1990, vol. 29, pp. 509-8517.*
Agostini, et al. *CD8 T-Cell Infiltration in Extravascular Tissues of Patients with Human Immunodeficiency Virus Infection. Interleukin-15 Upmodulates Costimulatory Pathways Involved in the Antigen-Presenting Cells-T-Cell Interaction*. Blood 93(4):1277-1286 (1999).
Anderson, et al. *Functional Characterization of the Human Interleukin-15 Receptor α Chain and Close Linkage of IL15RA and IL2RA Genes*. Journal of Biological Chemistry 270(5):29862-29869 (1995).
Bamford, et al. *The interleukin (IL) 2 receptor β chain is shared by IL-2 and a cytokine, provisionally designated IL-T, that stimulates T-cell proliferation and the induction of lymphokine-activated killer cells*. Proc. Natl. Acad. Sci. USA 91:4940-4944 (1994).
Burger, et al. *Imbalance between interstitial collagenase and tissue inhibitor of metalloproteinases 1 in synociocytes and fibroblasts upon direct contact with stimulated T Lymphocytes* Arthritis & Rheumatism 41(10):1748-1759 (1998).
Burton, et al. *A lymphokine, provisionally designated interleukin T and produced by a human adult T-cell leukemia line, stimulates T-cell proliferation and the induction of lymphokine-activated killer cells*. Proc. Natl. Acad. Sci. USA 91:4935-4939 (1994).
Carson, et al. *Interleukin (IL) 1 5 Is a Novel Cytokine That Activates Human Natural Killer Cells via Components of the IL-2 Receptor*. J. Exp. Med. 180:1395-1403 (1994).
Case, et al. *Chimeric cytoxin IL2-PE40 delays and mitigates adjuvant-induced arthritis in rats*. Proc. Natl. Acad. Sci. USA 86:287-291 (1989).
Chae, et al. *Distribution of IL-15 Receptor α-Chains on Human Peripheral Blood Mononuclear Cells and Effect of Immunosuppressive Drugs on Receptor Expression*. Journal of Immunology 157:2813-2819 (1996).
Chae, et al. *Mutant IL-15 Protein lexerting Antagonistic Effects on IL-15 Triggered Cell Proliferation*. JASN 7(9):1654 (1996).

(Continued)

*Primary Examiner*—Bridget E. Bunner
*Assistant Examiner*—Fozia M Hamud
(74) *Attorney, Agent, or Firm*—Fish & Richardson P.C.

(57) ABSTRACT

The present invention is based, in part, on expression studies of IL-2 and IL-15 receptor subunits by cycling T cells in vivo. In one embodiment, the invention generally features novel combinations of IL-2 and IL-15 antagonists and methods of suppressing the immune response by administering these antagonists. In each case, suppression is achieved by administration of a first agent that targets an IL-15 molecule or an IL-15 receptor (IL-15R) and a second agent that targets an IL-2 molecule or an IL-2 receptor (IL-2R). More generally, the invention features novel combinations of agents that, when administered to a patient (or to a transplant ex vivo), reduce the number of antigen-reactive T cells. For example, the invention features compositions (e.g., pharmaceutically acceptable compositions) that include two or more agents, each of which promote T cell death. Alternatively, the composition can contain at least one agent that promotes T cell death and at least one agent that inhibits T cell proliferation. The agent that promotes T cell death can promote AICD (activation induced cell death), passive cell death, ADCC (antibody dependent cell-mediated cytotoxicity) or CDC (complement directed cytotoxicity).

10 Claims, 20 Drawing Sheets

OTHER PUBLICATIONS

Chang et al., "Blocking the common gamma chain of cytokine receptors induces T cell apoptosis and long term islet allograft survival," *J. Immunol.* 164:1193-1199 (2000).

Courtenay, et al. *Immunisation against heterologous type II collagen induces arthritis in mice.* Nature 283(5748): 666-668 (1980).

Elliot, et al. *Repeated therapy with monoclonal antibody to tumor necrosis factor α (cA2) in patients with rheumatoid arthritis.* Lancet 344(8930):1125-1127 (1994).

Elliott, et al. *Randomized double-blind comparison of chimeric monoclonal antibody to tumour necrosis factor α (cA2) versus placebo in rheumatoid arthritis.* Lancet 344(8930):1105-1110 (1994).

Ferrari-Lacraz, et al. *An Antagonist IL-15/Fc Protein Prevents Costimulation Blockade-Resistant Rejection.* Journal of Immunology 167:3478-3485 (2001).

Giri, et al. *Utilization of the β and γ chains of the IL-2 receptor by the novel cytokine IL-15.* The EMBO Journal 13(12):2822-2830 (1994).

Giri, et al. *Identification and cloning of a novel IL-15 binding protein that is structurally related to the α chain of the IL-2 receptor.* The EMBO Journal 14(15):3654-3663 (1995).

Giri, et al. *IL-15, a novel T cell growth factor that shares activities and receptor components with IL-2.* Journal of Leukocyte Biology 57(5):763-766 (1995).

Grabstein, et al. *Cloning of a T Cell Growth Factor That Interacts with the β Chain of the Interleukin-2 Receptor.* Science 264:965-968 (1994).

Hatakeyama, et al. *A Restricted Cytoplasmic Region of IL-2 Receptor β Chain Is Essential for Growth Signal Transduction but Not for Ligand Binding and Internalization.* Cell 59:837-845 (1989).

Kim, et al. *Targeting the IL-15 Receptor with an Antagonist IL-15 Mutant/Fcγ2a Protein Blocks Delayed-Type Hypersensitivity.* Journal of Immunology 160:5742-5748 (1998).

Kim, et al. *Targeting the IL-15 Receptor with an Antagonist IL-15/Fcγ2a Protein BlocksDTH and Enhances the Acceptance of Islet Allografts.* 17$^{th}$ ASTP (Physicist) Annual Meeting, Chicago, IL May 9-13, 1998 (p. 713).

Kim, et al. *Immunoglobulin-Cytokine Fusion Molecules: The New Generation of Immunomodulating Agents.* Transplantation Proceedings 30:4031-4036 (1998).

Li, et al. *Blocking both signal 1 and signal 2 of T-cell activation prevents apoptosis of alloreactive T cells and induction of peripheral allograft tolerance.* Nature Medicine 5(11):1298-1302 (1999).

Li, et al. *Induction of Allograft Tolerance in the Absence of Fas-Mediated Apoptosis.* Journal of Immunology 163:2500-2507 (1999).

Lin, et al. *The Role of Shared Receptor Motifs and Common Stat Proteins in the Generation of Cytokine Pleiotropy and Redundancy by IL-2, IL-4, IL-7, IL-13, and IL-15.* Immunity, 2:331-339 (Apr. 1995).

Maslinski, et al. *Intoxication of high affinity IL-2 receptor positive thymocytes blocks early stages of T cell maturation.* International Immunology 4(4):509-517 (1992).

Maslinski, et al. *Interleukin-2 (IL-2) Induces Tyrosine Kinase-dependant Translocation of Active Raf-1 from the IL-2 Receptor into the Cytosol.* Journal of Biological Chemistry 267(22):15281-15284 (1992).

Moreland, et al. *Treatment of Rheumatoid Arthritis with a Recombinant Human Tumor Necrosis Factor Receptor (p75)-Fc Fusion Protein.* N. Engl. J. Med 337(3):141-147 (1997).

Morrison, et al. *Structural Determinants of Human IgG Function.* The Immunologist 2(4):119-124 (1994).

Pettit, et al. *Polyethylene Glycol Conjugation to Lysine Residues of Recombinant IL-15 Geenrates a Specific IL-15 Antagonist.* Proceed. Intern. Symp. Control. Rel. Bioact. Mater. 22:496-497 (1995).

Pettit, et al. *Structural-Function Studies of Interleukin 15 using Site-specific Mutagenesis, Polyethylene Glycol Conjugation, and Homology Modeling.* The Journal of Biologial Chemistry 272(4):2312-2318 (1997).

Remillard, et al. *Interleukin-2 Receptor Regulates Activation of Phosphatidylinositol 3- Kinase.* Journal of Biological Chemistry 266(22):14167-14170 (1991).

Stevens, et al. *Interleukin-15 signal, T84 colonic epithelial cells in the absence of the interleukin-2 receptor β-chain.* Am. J. Physiol. 272:G1-G8 (1997).

Stunkel, et al. *Monitoring of interleukin-2 receptor (IL-2R) expression* in vivo *and studies on an IL-2R-directed immunosuppressive therapy of active and adoptive adjuvant-induced arthritis in rats.* Immunology 64:683-689 (1988).

Vey, et al. *IFN-γ and 1,25(OH)hd 2D$_3$ Induce on THP-1 Cells Distinct Patterns of Cell Surface Antigen Expression, Cytokine Production, and Responsiveness to Contact with Activated T Cells.* Journal of Immunology 149(6):2040-2046 (1992).

Williams, et al. *Design, synthesis and expression of a human interleukin-2 gene incorporating the codon usage bias found in highly expressed Escherichia coli genes.* Nucleic Acids Research 16(22):10453-10467 (1988).

Williams, et al. *Structure/Function Analysis of Interleukin-2-Toxin (DAB$_{486}$-IL-2).* Journal of Biological Chemistry 265(20):11885-1189 (1990).

Williams, et al. *Successful therapy of collagen-induced arthritis with TNF receptor-IfG fusion protein and combination with anti-CD4.* Immunology 84(3): 433-439 (1995).

Wooley, et al. *Influence of a Recombinant Human Soluble Tumor Necrosis Factor Receptor FC Fusion Protein on Type II Collagen-Induced Arthritis in Mice.* Journal of Immunology 151(11):6442-6607 (1993).

Zurawski, et al. *Definition and spatial location of mouse interleukin-2 residues that interact with its heterotrimeric receptors.* The EMBO Journal 12(13):513-5119 (1993).

Bulfone-Paus, et al., "Differential regulation of human T lymphoblast functions by IL-2 and IL-15," Cytokine, 9(7):507-513 (1997).

Guex-Corsier, et al., "Humanized anti-IL-2 and anti-IL-15 receptor antibodies in the treatment of uveorentinitis in a monkey model," Invest. Opthal. & Visual Sci., 37(3):S896 (1996).

Rueckert, et al., "IL-15, IgG2b fusion protein accelerates and enhances a Th2 but not a Th1 immune response in vivo, while IL-2-IgG2b fusion protein inhibits both," Eur. J. Immunol., 28(10):3312-3320 (1998).

Tinubu, et al., "Humanized Antibody Directed to the IL-2 Receptor Beta-Chain Prolongs Primate Cardiac Allograft Survival," J. Immunol., 153:4330-4338 (1994).

Waldmann, et al., "The use of antibodies against the IL-2 receptor in transplantation," Curr. Opin. Immunol., Curr. Biol. Ltd., 10(5):507-512 (1998).

Zheng, et al., "IL-2-receptor-targeted cytolytic IL-2/Fc fusion protein treatment blocks diabetogenic autoimmunity in nonobese diabetic mice," J. Immunol., 163(7):4041-4048 (1999).

Morelon et al., "Sirolimus: a new promising immunosuppressive drug. Towards a rationale for its use in renal transplantation" *Nephrol Dial Translpant* 16:18-20 (2001).

Phillips et al., "IL-2Rα-Directed Monoclonal Antibodies Provide Effective Therapy in a Murine Model of Adult T-Cell Leukemia by a Mechanism other than Blockade of IL-2/ IL-2Rα Interaction" *Cancer Res.* 60:6977-6984 (2000).

Armitage, et al. *IL-15 Has Stimulatory Activity for the Induction of B Cell Proliferation and Differentiation.* Journal of Immunology 154:483-490 (1995).

Brekke, et al. *Structure-Function Relationships of Human IgG.* The Immunologist 2(4):125-130 (1994).

\* cited by examiner

DNA sequence 489 b.p. atgagaatttcg ... aacacttcttga  linear

```
1/1
atg aga att tcg aaa cca cat ttg aga agt att tcc atc cag tgc tac ttg tgt tta ctt
Met arg ile ser lys pro his leu arg ser ile gln cys tyr leu cys leu leu
 61/21
cta aac agt cat ttt cta act gaa gct ggc att cat gtc ttc att ttg ggc tgt ttc agt
leu asn ser his phe leu thr glu ala gly ile his val phe ile leu gly cys phe ser
121/41
gca ggg ctt cct aaa aca gaa gcc aac tgg gtg aat gta ata agt gat ttg aaa aaa att
ala gly leu pro lys thr glu ala asn trp val asn val ile ser asp leu lys lys ile
181/61
gaa gat ctt att caa tct atg cat att gat gct act tta tat acg gaa agt gat gtt cac
glu asp leu ile gln ser met his ile asp ala thr leu tyr thr glu ser asp val his
241/81
ccc agt tgc aaa gta aca gca atg aag tgc ttt ctc ttg gag tta caa gtt att tca ctt
pro ser cys lys val thr ala met lys cys phe leu leu glu leu gln val ile ser leu
301/101
gag tcc gga gat gca agt att cat gat aca gaa aat ctg atc atc cta gca aac aac
glu ser gly asp ala ser ile his asp thr glu asn leu ile ile leu ala asn asn
361/121
agt ttg tct tct aat ggg aat gta aca gaa tct gga tgc aaa gaa tgt gag gaa ctg gag
ser leu ser ser asn gly asn val thr glu ser gly cys lys glu cys glu glu leu glu
421/141
gaa aaa aat att aaa gaa ttt ttg gac agt ttt gta cat att gtc gac atg ttc atc aac
glu lys asn ile lys glu phe leu asp ser phe val his ile val asp met phe ile asn
481/161
act tct tga        (SEQ ID NO:1)
thr ser OPA        (SEQ ID NO:2)
```

FIG. 1

DNA sequence 489 b.p. atgagaatttcg ... aacacttcttga linear

```
1/1                                                              31/11
atg aga att tcg aaa cca cat ttg aga agt att tcc atc cag tgc tac ttg tgt tta ctt
Met arg ile ser lys pro his leu arg ser ile ser ile gln cys tyr leu cys leu leu
61/21                                                            91/31
cta aac agt cat agt ttt cta act gaa gct ggc att cat gtc ttc att ttg ggc tgt ttc agt
leu asn ser his ser phe leu thr glu ala gly ile his val phe ile leu gly cys phe ser
121/41                                                           151/51
gca ggg ctt cct aaa aca gaa gcc aac tgg gtg aat gta ata agt gat ttg aaa aaa att
ala gly leu pro lys thr glu ala asn trp val asn val ile ser asp leu lys lys ile
181/61                                                           211/71
gaa gat ctt att caa tct atg cat att gat gct act tta tat acg gaa agt gat gtt cac
glu asp leu ile gln ser met his ile asp ala thr leu tyr thr glu ser asp val his
241/81                                                           271/91
ccc agt tgc aaa gta aca gca atg aag tgc ttt ctc ttg gag tta caa gtt att tca ctt
pro ser cys lys val thr ala met lys cys phe leu leu glu leu gln val ile ser leu
301/101                                                          331/111
gag tcc gga gat gca agt att cat gat aca gta gaa aat ctg atc atc cta gca aac aac
glu ser gly asp ala ser ile his asp thr val glu asn leu ile ile leu ala asn asn
361/121                                                          391/131
agt ttg tct tct aat ggg aat gta aca gaa tct gga tgc aaa gaa tgt gag gaa ctg gag
ser leu ser ser asn gly asn val thr glu ser gly cys lys glu cys glu glu leu glu
421/141                                                          451/151
gaa aaa aat att aaa gaa ttt ttg cag agt ttt gta cat att gtc caa atg ttc atc aac
glu lys asn ile lys glu phe leu gln ser phe val his ile val gln met phe ile asn
481/161
act tct tga (SEQ ID NO:3)
thr ser OPA (SEQ ID NO:4)
```

FIG. 2

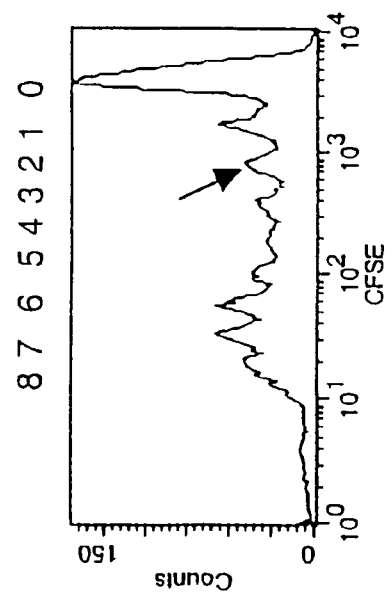
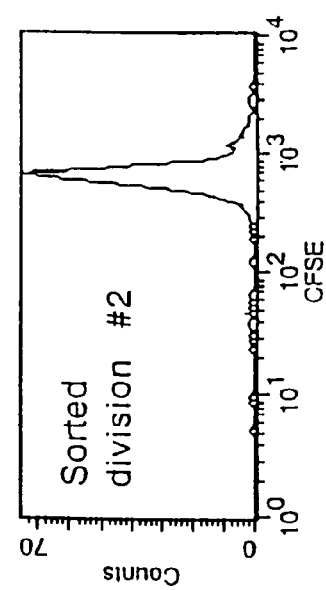
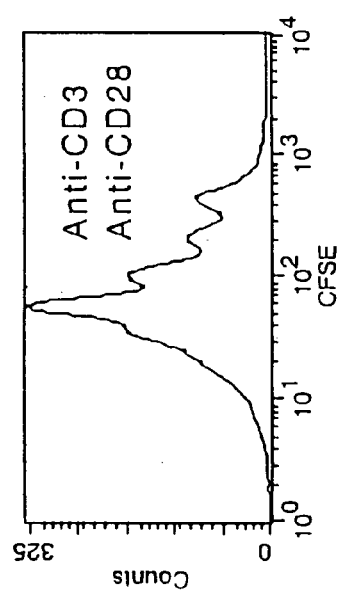
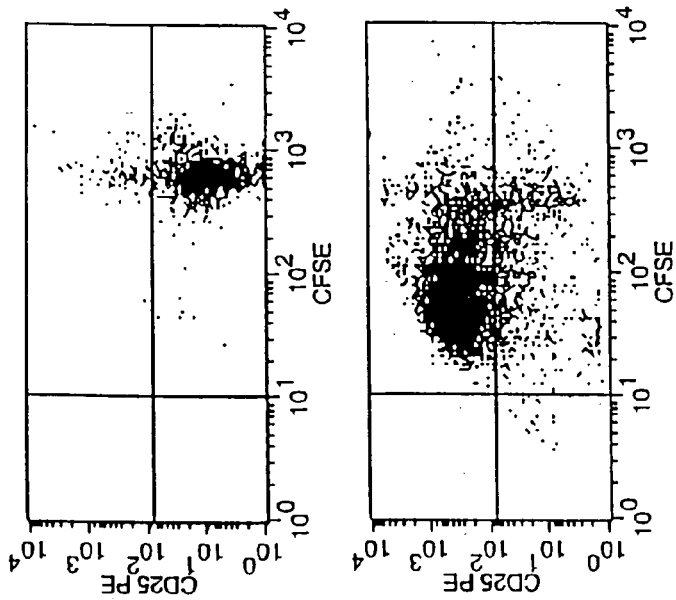
FIG. 3D

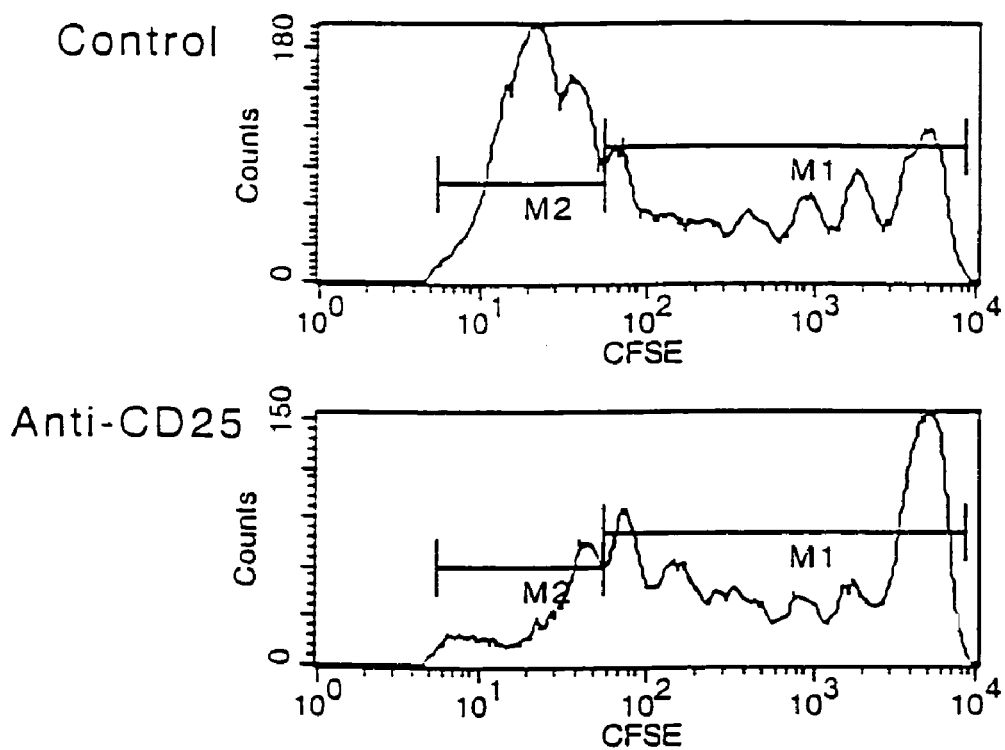
FIG. 4C
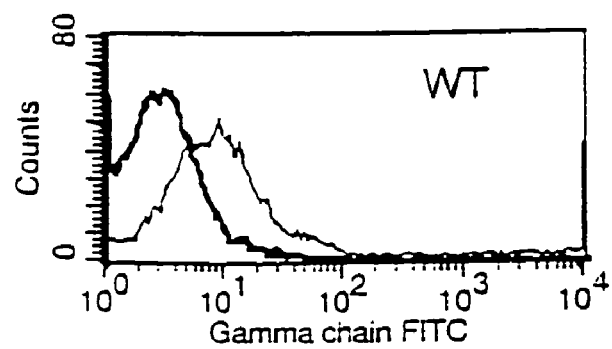
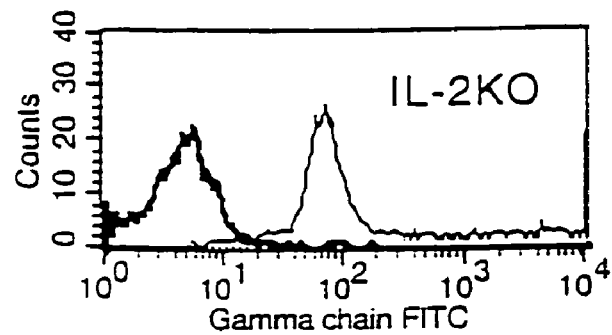
FIG. 5B

| Treatment | 1° Allograft Function | MST of Functioning Grafts | n |
|---|---|---|---|
| no-Treatment | 40% | 6 | 7 |
| Rapamycin* | 50% | 12 | 6 |
| MR1+CTLA4/Fc+ Rapamycin** | 75% | 30 | 4 |
| Lytic IL-2/Fc+mIL-15/Fc+ Rapamycin*** | 100% | >110 | 5 |
| Non-lytic IL-2/Fc+mIL-15/Fc +Rapamycin*** | 50% | 16 | 4 |

\* Rapamycin treatment was initiated 7 day prior to transplantation with 3 mg/kg i.p. daily for 7 days and continued every other day for 4 wks.. DBA2 mice were used as islet allograft donors.

\*\* MR1 treatment was administrated on day -7, -5, -3, 0 to transplantation at a dose of 0.25 mg i.p.. CTLA4/Fc treatment was administrated on day -7, -5, -3, 0 to transplantation at a dose of 0.2 mg i.p..

\*\*\* IL-2/Fc, and mutant IL-15/Fc treatment was initiated 7 day prior to transplantation for 4 weeks. IL-2/Fc and mutant IL-15/Fc treatment was given at a dose of 5 μg i.p. daily for 4 weeks.

FIG. 11

| Tr atment | MST of Functioning Grafts | n |
|---|---|---|
| no-Treatment | 15 | 4 |
| Rapamycin* | 17 | 4 |
| Rapamycin + MR1+CTLA4/Fc** | 25 | 4 |
| Rapamycin + Lytic IL-2/Fc*** | 22 | 4 |
| Rapamycin + Lytic mutant IL-15/Fc*** | 18 | 3 |
| Rapamycin + Lytic IL-2/Fc+ mutant IL-15/Fc*** | >60 | 6 |

\* Rapamycin treatment was initiated at the day of transplantation with 3 mg/kg i.p daily for 7 days and continued every other day for 4 wks. DBA2 mice were used as skin allograft donors.

\*\* MR1 treatment was administered on day 0, 2, 4, 6 to transplantation at a dose of 0.25 mg i.p. . CTLA4/Fc treatment was administrated on day 0, 2, 4, 6 to transplantation at a dose of 0.2 mg i.p. .

\*\*\* IL-2/Fc, and mutant IL-15/Fc treatment was initiated on the day of transplantation with a dose of at 5 µg i.p. daily for 4 weeks.

FIG. 12

SEQUENCE LISTING

```
<160> NUMBER OF SEQ ID NOS: 7

<210> SEQ ID NO 1
<211> LENGTH: 489
<212> TYPE: DNA
<213> ORGANISM: Homo sapiens
<220> FEATURE:
<221> NAME/KEY: CDS
<222> LOCATION: (1)...(486)

<400> SEQUENCE: 1 atg aga att tcg aaa cca cat ttg aga agt att tcc atc cag tgc tac      48
Met Arg Ile Ser Lys Pro His Leu Arg Ser Ile Ser Ile Gln Cys Tyr
  1               5                  10                  15 ttg tgt tta ctt cta aac agt cat ttt cta act gaa gct ggc att cat      96
Leu Cys Leu Leu Leu Asn Ser His Phe Leu Thr Glu Ala Gly Ile His
             20                  25                  30 gtc ttc att ttg ggc tgt ttc agt gca ggg ctt cct aaa aca gaa gcc     144
Val Phe Ile Leu Gly Cys Phe Ser Ala Gly Leu Pro Lys Thr Glu Ala
         35                  40                  45 aac tgg gtg aat gta ata agt gat ttg aaa aaa att gaa gat ctt att     192
Asn Trp Val Asn Val Ile Ser Asp Leu Lys Lys Ile Glu Asp Leu Ile
     50                  55                  60 caa tct atg cat att gat gct act tta tat acg gaa agt gat gtt cac     240
Gln Ser Met His Ile Asp Ala Thr Leu Tyr Thr Glu Ser Asp Val His
 65                  70                  75                  80 ccc agt tgc aaa gta aca gca atg aag tgc ttt ctc ttg gag tta caa     288
Pro Ser Cys Lys Val Thr Ala Met Lys Cys Phe Leu Leu Glu Leu Gln
                 85                  90                  95 gtt att tca ctt gag tcc gga gat gca agt att cat gat aca gta gaa     336
Val Ile Ser Leu Glu Ser Gly Asp Ala Ser Ile His Asp Thr Val Glu
            100                 105                 110 aat ctg atc atc cta gca aac aac agt ttg tct tct aat ggg aat gta     384
Asn Leu Ile Ile Leu Ala Asn Asn Ser Leu Ser Ser Asn Gly Asn Val
        115                 120                 125 aca gaa tct gga tgc aaa gaa tgt gag gaa ctg gag gaa aaa aat att     432
Thr Glu Ser Gly Cys Lys Glu Cys Glu Glu Leu Glu Glu Lys Asn Ile
    130                 135                 140 aaa gaa ttt ttg gac agt ttt gta cat att gtc gac atg ttc atc aac     480
Lys Glu Phe Leu Asp Ser Phe Val His Ile Val Asp Met Phe Ile Asn
145                 150                 155                 160 act tct tga                                                         489
Thr Ser

<210> SEQ ID NO 2
<211> LENGTH: 162
<212> TYPE: PRT
<213> ORGANISM: Homo sapiens
```

<400> SEQUENCE: 2

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
130                 135                 140

Lys Glu Phe Leu Asp Ser Phe Val His Ile Val Asp Met Phe Ile Asn
145                 150                 155                 160

Thr Ser

<210> SEQ ID NO 3
<211> LENGTH: 489
<212> TYPE: DNA
<213> ORGANISM: Homo sapiens
<220> FEATURE:
<221> NAME/KEY: CDS
<222> LOCATION: (1)...(486)

<400> SEQUENCE: 3 atg aga att tcg aaa cca cat ttg aga agt att tcc atc cag tgc tac      48
Met Arg Ile Ser Lys Pro His Leu Arg Ser Ile Ser Ile Gln Cys Tyr
1               5                   10                  15 ttg tgt tta ctt cta aac agt cat ttt cta act gaa gct ggc att cat      96
Leu Cys Leu Leu Leu Asn Ser His Phe Leu Thr Glu Ala Gly Ile His
            20                  25                  30 gtc ttc att ttg ggc tgt ttc agt gca ggg ctt cct aaa aca gaa gcc      144
Val Phe Ile Leu Gly Cys Phe Ser Ala Gly Leu Pro Lys Thr Glu Ala
        35                  40                  45 aac tgg gtg aat gta ata agt gat ttg aaa aaa att gaa gat ctt att      192
Asn Trp Val Asn Val Ile Ser Asp Leu Lys Lys Ile Glu Asp Leu Ile
    50                  55                  60 caa tct atg cat att gat gct act tta tat acg gaa agt gat gtt cac      240
Gln Ser Met His Ile Asp Ala Thr Leu Tyr Thr Glu Ser Asp Val His
65                  70                  75                  80 ccc agt tgc aaa gta aca gca atg aag tgc ttt ctc ttg gag tta caa      288
Pro Ser Cys Lys Val Thr Ala Met Lys Cys Phe Leu Leu Glu Leu Gln
                85                  90                  95 gtt att tca ctt gag tcc gga gat gca agt att cat gat aca gta gaa      336
Val Ile Ser Leu Glu Ser Gly Asp Ala Ser Ile His Asp Thr Val Glu
            100                 105                 110 aat ctg atc atc cta gca aac aac agt ttg tct tct aat ggg aat gta      384
Asn Leu Ile Ile Leu Ala Asn Asn Ser Leu Ser Ser Asn Gly Asn Val
        115                 120                 125 aca gaa tct gga tgc aaa gaa tgt gag gaa ctg gag gaa aaa aat att      432
Thr Glu Ser Gly Cys Lys Glu Cys Glu Glu Leu Glu Glu Lys Asn Ile -continued

```
aaa gaa ttt ttg cag agt ttt gta cat att gtc caa atg ttc atc aac      480
Lys Glu Phe Leu Gln Ser Phe Val His Ile Val Gln Met Phe Ile Asn
145                 150                 155                 160 act tct tga                                                          489
Thr Ser
```

<210> SEQ ID NO 4
<211> LENGTH: 162
<212> TYPE: PRT
<213> ORGANISM: Homo sapiens

<400> SEQUENCE: 4

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
        50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
130                 135                 140

Lys Glu Phe Leu Gln Ser Phe Val His Ile Val Gln Met Phe Ile Asn
145                 150                 155                 160

Thr Ser
```

<210> SEQ ID NO 5
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 5
ggaattcaac tgggtgaatg taata                                          25

<210> SEQ ID NO 6
<211> LENGTH: 26
<212> TYPE: DNA
<213> ORGANISM: Artificial Sequence
<220> FEATURE:
<223> OTHER INFORMATION: Synthetically generated oligonucleotide

<400> SEQUENCE: 6
cgggatcctc aagaagtgtt gatgaa                                         26

<210> SEQ ID NO 7
<211> LENGTH: 60
<212> TYPE: DNA
<213> ORGANISM: Artificial Sequence
<220> FEATURE:

-continued

```
<223> OTHER INFORMATION: Synthetically generated oligonucleotide

<400> SEQUENCE: 7
cgggatcctc aagaagtgtt gatgaacatg tcgacaatat gtacaaaact gtccaaaaat      60
```

MODULATION OF IL-2- AND IL-15-MEDIATED T CELL RESPONSES

RELATED APPLICATIONS

This application is a continuation (and claims the benefit of priority under 35 USC 120) of U.S. application Ser. No. 10/749,699, filed Dec. 30, 2003, which is a continuation of U.S. application Ser. No. 09/953,323, filed Sep. 14, 2001 (now abandoned), which claims the benefit of U.S. application Ser. No. 60/232,251, filed Sep. 14, 2000 (now expired). The disclosures of the prior applications are considered part of (and are incorporated by reference in) the disclosure of this application.

FEDERALLY SPONSORED RESEARCH

The work described herein was supported in part by a grant from the National Institutes of Health. The United States government may, therefore, have certain rights in the invention.

TECHNICAL FIELD

This invention relates to immunology, transplant rejection, and diseases associated with the immune system.

BACKGROUND

Two of the interleukins, IL-2 and IL-15, are functionally redundant in stimulating T cell proliferation in vitro. However, their role in primary immune activation and immune homeostasis in vivo is much less clear. In vivo, IL-2 and IL-15 may have distinct functions and regulate distinct aspects of T cell activation. For example, IL-2 may prime activated T cells for apoptosis (Lenardo, Nature 353:858-861, 1991), while IL-15 may support cell survival (Dooms et al., J. Immunol. 161:2141-2150, 1998; Bulfone et al. Nature Medicine 3:1124-1128, 1997). IL-15 also appears to drive the proliferation of memory type $CD8^+$ T cells in vivo while IL-2 limits their continued expansion (Ku et al., Science 288:675-678, 2000). In addition, the phenotype of IL-2 deficient mice is lymphoproliferative and autoimmune (Horak et al., Immunol. Rev. 148:35-44, 1995), whereas IL-15 deficient mice are somewhat lymphopenic and unable to mount a primary response to viral challenge (Kennedy et al., J. Exp. Med. 191:771-780, 2000; Lodolce et al., Immunity 9:669-676, 1998). The molecular basis for this striking dichotomy remains enigmatic.

The functional receptors for IL-2 and IL-15 consist of a private α chain, which defines the binding specificity for IL-2 or IL-15, and shared IL-2 receptor β and γ chains. The γ chain is also a critical signaling component of the IL-4, IL-7, and IL-9 receptors (Sugamura et al., Ann. Rev. Immunol. 14:179-205, 1996). In the lymphoid compartment, these receptor subunits can be expressed individually or in various combinations resulting in the formation of receptors with different affinities and/or with distinct signaling capabilities (Sugamura et al., supra). For example, the β chain can associate with either the α chain or the γ chain to form dimeric structures, or with both the α and γ chains to form trimeric structures. Similarly, the γ chain can interact with the β chain and, through the β chain, with the α chain of either the IL-2 receptor or the IL-15 receptor. The IL-15 receptor α chain alone, in contrast to the IL-2 receptor α chain, can bind to IL-15 with a remarkably high affinity (Giri et al., EMBO J. 14:3654-3663, 1995). However, similar to IL-2 receptor α chain, this interaction is not believed to trigger signaling events. Thus, trimerization of α, β, and γ chain subunits is essential for the functional integrity of high affinity receptors for both IL-2 and IL-15.

In vitro studies have shown that activated T cells can express both IL-2 receptor α chain and IL-15 receptor α chain (Chae et al., J. Immunol. 157:2813-2819, 1996) and the β and γ chains are constitutively expressed by activated T cells (Ishii et al., Int. Immunol. 6:1273-1277, 1994). Furthermore, both IL-2 and IL-15 are readily detected during immune activation in vivo (Li et al., J. Immunol. 161:890-896, 1998). Thus, it is unclear how activated T cells distinguish between IL-2, IL-15, and other γ chain dependent cytokines in vivo.

SUMMARY

The present invention is based, in part, on expression studies of IL-2 and IL-15 receptor subunits by cycling T cells in vivo. Surprisingly, these subunits direct activated T cell responses to IL-2 or IL-15 in a selective manner and, thereby, regulate the T cell response in vivo. In other words (and contrary to the conventional wisdom that IL-2 and IL-15 are redundant), IL-2 and IL-15 perform different roles in controlling T cell proliferation in vivo. In particular, IL-15 is critical for initiating T cell division, whereas IL-2 controls T cell expansion via down-regulation of γc expression. Accordingly, in one embodiment, the invention generally features novel combinations of IL-2 and IL-15 antagonists and methods of suppressing the immune response by administering these antagonists. In each case, suppression is achieved by administration of a first agent that antagonizes an IL-15 molecule or an IL-15 receptor (IL-15R) and a second agent that antagonizes an IL-2 molecule or an IL-2 receptor (IL-2R). In alternative embodiments, the compositions of the invention can include (in place of, or in addition to, the agents described above), agents that inhibit the expression of the nucleic acids (e.g., DNA or RNA) that encode an interleukin (e.g., IL-2 or IL-15) or an interleukin receptor (e.g., an IL-2 or an IL-15 receptor).

More generally, the invention features novel combinations of agents that, when administered to a patient, reduce the number of antigen-reactive T cells. For example, the invention features compositions (e.g., pharmaceutically acceptable compositions) that include two or more agents, each of which promote T cell death. Alternatively, the composition can contain at least one agent that promotes T cell death and at least one agent that inhibits T cell proliferation. The agent that promotes T cell death can promote AICD (activation induced cell death), passive cell death, ADCC (antibody dependent cell-mediated cytotoxicity) or CDC (complement directed cytotoxicity).

Agents that promote AICD include IL-2 and related molecules (e.g., IL-2/Fc or other molecules that function as agonists of IL-2 or the IL-2 receptor (e.g., an antibody that specifically binds to the IL-2 receptor and mimics the binding of the receptor's natural ligand)). Another agent that promotes AICD is the Fas Ligand (FasL). Agents that promote passive cell death include agents that antagonize IL-1S (by targeting, e.g., binding to, and thereby inhibiting the activity of, IL-15, an IL-15 receptor, or a component of the intracellular signaling pathway that is activated once a receptor is bound) or any other factor required for T cell survival (e.g., IL-4, IL-7, OX-4 ligand, IFN-β, 4-1BB, or IGF-I). In alternative embodiments, the compositions of the invention can include (in place of, or in addition to, one or more of the agents described above), agents that inhibit the expression of the nucleic acids (e.g., DNA or RNA) that encode an interleukin (e.g., IL-2 or IL-15) or an interleukin receptor (e.g., an IL-2 or an IL-15 receptor).

One can promote ADCC or CDC by exposing a T cell to an agent that binds to the T cell surface and contains an Fc portion that activates ADCC or CDC. More specifically, agents that promote ADCC or CDC include fusion proteins that contain an interleukin (e.g., IL-2 or a mutant IL-15) and an Fc region (e.g., IL-2/Fc) as well as antibodies or other Fc-containing proteins that bind to an interleukin receptor (e.g., an IL-2 or an IL-15 receptor).

As stated above, the compositions of the invention can include not only an agent that promotes T cell death, but also an agent that inhibits T cell proliferation. Agents that inhibit T cell proliferation include rapamycin, mycophenolate mofetil (MMF), azathioprine, and any of the other agents known and used in the art to prevent cellular proliferation (including chemotherapeutic agents). The use of an agent that inhibits T cell proliferation is particularly useful in combination with agents that promote AICD and also stimulate T cell proliferation (such as IL-2/Fc). For example, the invention features a pharmaceutically acceptable composition that includes IL-2/Fc (which, for example, promotes AICD and cellular lysis via ADCC or CDC), an IL-15 antagonist (which, for example, promotes passive cell death by antagonizing IL-15, a factor required for T cell survival), and rapamycin (which inhibits T cell proliferation). Compositions containing other combinations of agents are described below.

Notably, when two or more agents are employed, they need not be physically separate from one another. While an agent can be a single entity that has primarily one functional activity (e.g., an antibody that targets IL-2 or IL-15 by specifically binding IL-2 or IL-15), it can also be a single entity that has at least two functional activities (e.g., IL-2/Fc, mIL-15/Fc, or an anti-IL-2 or anti-IL-15 antibody; in these molecules, the interleukin mediates AICD and the Fc portion of the molecule mediates CDC and ADCC). Thus, a composition that includes (1) an agent that induces AICD, (2) an agent that induces CDC, and (3) an agent that inhibits cellular proliferation may include only two active ingredients (e.g., (1) an IL-2/Fc molecule, which induces AICD and CDC, and (2) rapamycin, which inhibits cellular proliferation).

The compositions described herein are useful in treating patients who would benefit from immune suppression (e.g., a patient who has received, or is scheduled to receive, a transplant; a patient who has an immune disease, particularly an autoimmune disease; a patient who has cancer (e.g., a cancer of the immune system), or a patient suffering from graft versus host disease (GVHD)). GVHD is characterized by a response of donor leukocytes against antigens in the recipient. This response is particularly problematic in bone marrow transplants, but also occurs in whole organ transplants; donor leukocytes resident in transplanted organs are always co-transplanted.

Although the compositions of the invention can contain more than one agent, the methods of the invention are not limited to those in which the agents are administered simultaneously. For example, a patient could receive a composition containing an IL-15 antagonist or an IL-15R antagonist before receiving a composition containing an IL-2 antagonist or an IL-2R antagonist. Similarly, a patient could receive a composition containing rapamycin before receiving a composition containing an IL-2 agonist. Moreover, the compositions of the invention (applied simultaneously or sequentially) can be used to treat an organ or cellular graft before it is implanted in a patient. The agents of the invention, and methods for their use, are described further below.

Many of the agents used in the context of the present invention have advantageous therapeutic characteristics. For example, agents that target an IL-15R can be fusion proteins that include a mutant IL-15 (mIL-15) polypeptide. These agents are unlikely to be immunogenic because the mutant IL-15 portion of the fusion protein can differ from wild type IL-15 by only a few substituted residues. In addition, since mIL-15 polypeptides can bind the IL-15Rα with high affinity, they can compete effectively with wild type IL-15 for the receptor. Further, agents of the invention can activate components of the host immune system, such as complement and phagocytes, which ultimately mediate elimination of (or depletion of) cells bearing the receptor (e.g., an IL-2 receptor) to which the agent binds. For example, agents of the invention can mediate lysis or phagocytosis of targeted cells. As the alpha subunit of the IL-15 receptor (IL-15Rα) is expressed by activated or malignant immune cells, but not by resting immune cells, agents of the invention can be used to specifically target those cells that have been activated (e.g., antigen-activated T cells) or that have become malignant. Thus, although T cells represent a preferred target for the agents of the invention, the compositions of the invention can also be used to target other cells involved in the pathogenesis of immunological disorders, such as other cells of the immune system or hyperproliferating cells of tissues.

Unless otherwise defined, all technical and scientific terms used herein have the same meaning as commonly understood by one of ordinary skill in the art to which this invention belongs. All publications, patent applications, patents and other references mentioned herein are incorporated by reference in their entirety.

Other features and advantages of the invention will be apparent from the drawings, the detailed description, and claims. Although materials and methods similar or equivalent to those described herein can be used in the practice or testing of the invention, the preferred materials and methods are described below.

BRIEF DESCRIPTION OF THE DRAWINGS

FIG. 1 is a representation of a mutant IL-15 nucleic acid sequence (SEQ ID No:1) and the predicted amino acid sequence (SEQ ID NO:2).

FIG. 2 is a representation of a wild-type IL-15 nucleic acid sequence (SEQ ID NO:3) and the predicted amino acid sequence (SEQ ID NO:4). The wild-type codon encoding glutamine at position 149, CAG, and the wild-type codon encoding glutamine at position 156, CAA, are both changed to GAC, which encodes aspartate, in the mutant sequence shown in FIG. 1. (These positions (149 and 156) correspond to positions 101 and 108, respectively, in the mature IL-15 polypeptide, which lacks a 48-amino acid signal sequence).

FIG. 3D is a series of plots depicting differential expression of IL-2 receptor α chain between in vivo dividing T cells. CFSE-labeled cells were stimulated in vivo for three days and cells in the second cell division were sorted. The sorted cells were re-stimulated in vitro with anti-CD3 and anti-CD28 for three days. Cells division and expression of the IL-2 receptor α chain were analyzed by FACS.

FIG. 4C is a pair of graphs depicting the effect of anti-CD25 treatment on T cell division in vivo. Host mice were given anti-CD25 mAb intraperiotoneally (i.p.) at 1 mg/day for three days immediately before intravenous injection of CFSE-labeled cells. Mice treated with isotype control mAb (rat IgG1) were included as a control.

FIG. 5B is a pair of graphs depicting expression of γc by CD4$^+$ T cells from IL-2 deficient mice. Spleen cells from IL-2 deficient mice and wild type control mice were stained with PE-anti-mouse CD4mAb and FITC-anti-mouse IL-2 receptor γc mAb. The expression of γc by CD4$^+$T cells was analyzed by FACS.

FIG. 11 is a Table showing the results of experiments that examined islet allograft survival in autoimmune non-obese diabetic (NOD) mice. The grafts were assessed in terms of primary allograft function (the percentages shown in this column represent the percentage of mice in which the allograft functioned (function was assessed by monitoring blood gluocose levels)) and the mean survival time (MST) of the functioning grafts. n=the number of animals tested. The treatments are indicated under the heading "Treatment" (see also the legend that accompanies the Table and the description below). The results presented here support the conclusion that treatment with a combination of rapamycin, IL-2/Fc and mIL-15/Fc results in long-term survival of islet allografts.

FIG. 12 is a Table showing the results of experiments that examined the survival of skin allografts in NOD mice. The grafts were assessed in terms of the mean survival time (MST) of functioning grafts. n=the number of animals tested. The treatments are indicated under the heading "Treatment" (see also the legend that accompanies the Table and the description below). The results presented here support the conclusion that treatment with a combination of rapamycin, IL-2/Fc and mIL-15/Fc results in long-term survival of skin allografts.

DETAILED DESCRIPTION

Figure 3A:
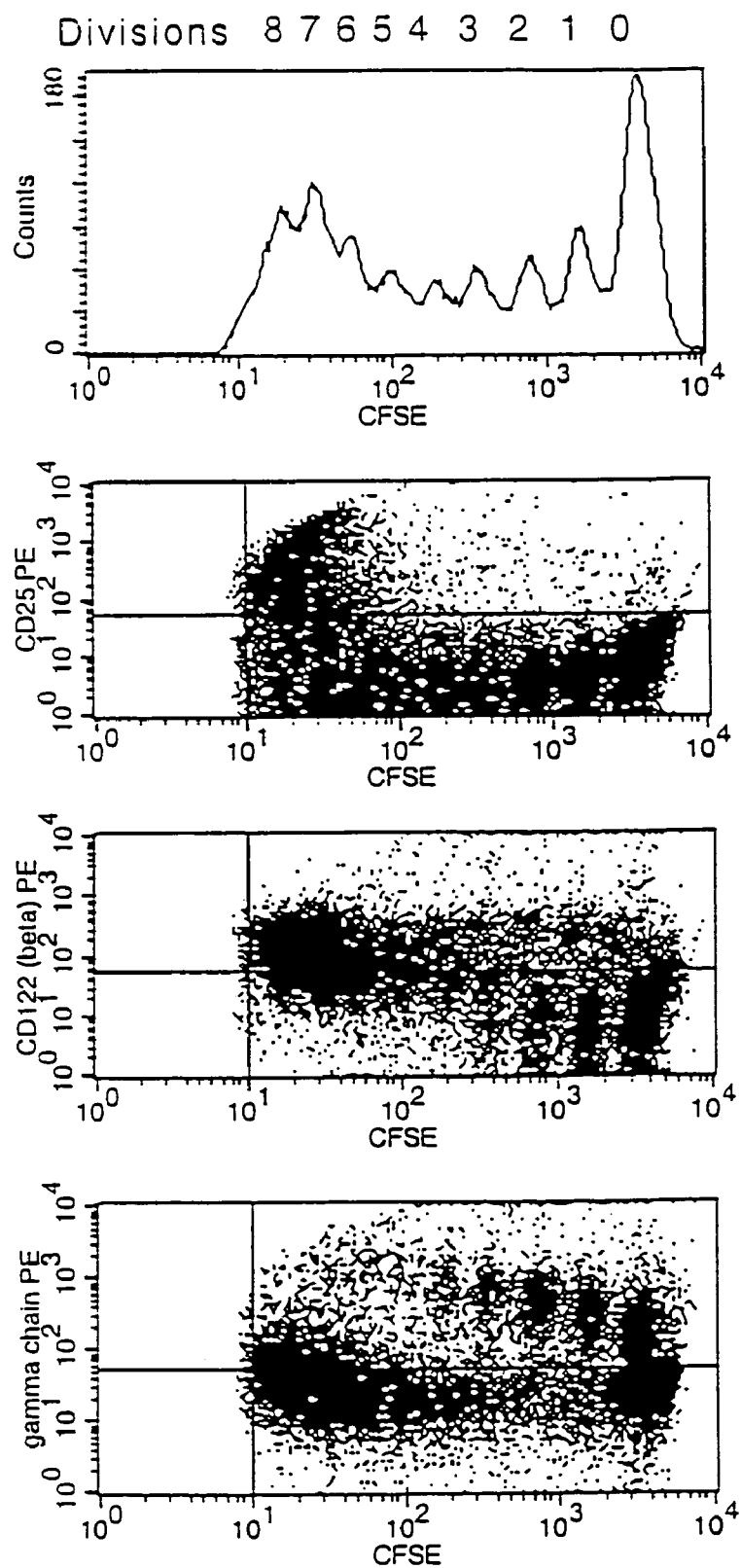
FIG. 3A is a series of plots depicting expression of IL-2 receptor α, β and γc chains by dividing T cells in a host spleen 3 days after intravenous (i.v.) injection of CFSE-labeled cells. Representative data of six experiments are shown.

An effective immune response begins when an antigen or mitogen triggers the activation of T cells. In the process of T cell activation, numerous cellular changes occur, which include the expression of cytokines and cytokine receptors. One of the cytokines involved in the immune response is interleukin-15 (IL-15), which is a T cell growth factor that stimulates the proliferation and differentiation of B cells, T cells, natural killer (NK) cells, and lymphocyte-activated killer (LAK) cells in vitro. In vivo, the proliferation of these cell types enhances the immune response. Another cytokine involved in the immune response, and described herein, is IL-2.

The compositions of the present invention include agents that target IL-15, or its receptor, and IL-2, or its receptor, and methods in which those compositions are used to suppress an immune response (e.g., a humoral or cellular immune response). Patients benefit from suppression of the immune response in a number of circumstances, for example, in the event of organ transplantation or immune disease, particularly autoimmune disease, or Graft Versus Host Disease. In other circumstances, for example when select immune cells have become malignant or autoaggressive, it is beneficial to actively destroy them.

The present invention is based on the discovery of novel ways to inhibit the immune response. Inhibition can be achieved by administering of a combination of agents, one of which targets IL-15 or an IL-15R and one of which targets IL-2 or an IL-2R (modes of administration, including ex vivo treatment of grafts, are known in the art and described further below). More generally, one can reduce the number of antigen-reactive T cells by activating signaling pathways that lead to the death of activated T cells (by, e.g., AICD); depriving cells of factors that are required for their survival (cells that die following such deprivation are said to die by passive cell death); or targeting activated cells for lysis by components of the immune system (cells that die in this way are said to die by ADCC or CDC). Accordingly, the compositions of the invention include agents that achieve one or more of these ends (i.e., that promote T cell death via a recognized cell death pathway (e.g., AICD, passive cell death, ADCC, or CDC)). In addition to containing one or more agents that promote T cell death, the compositions of the invention can include one or more agents that inhibit T cell proliferation (as occurs, e.g., in response to an antigen). For example, the invention features a composition (e.g., a pharmaceutically acceptable composition or one formulated for application to an organ or cell culture) that includes IL-2/Fc (which, for example, promotes AICD and cellular lysis via ADCC or CDC), mIL-15/Fc (which antagonizes IL-15 (and thereby promotes passive cell death) and promotes cellular lysis via ACDD or CDC), and rapamycin (which inhibits T cell proliferation).

The term "agent" is meant to encompass essentially any type of molecule that can be used as a therapeutic agent. Proteins, such as antibodies, fusion proteins, and soluble ligands, any of which may either be identical to a wild-type protein or contain a mutation (i.e., a deletion, addition, or substitution of one or more amino acid residues), and the nucleic acid molecules that encode them (or that are "antisense" to them; e.g., an oligonucleotide that is antisense to the nucleic acids that encode IL-2, IL-15, or a component (e.g., a subunit) of their receptors), are all "agents." The agents of the invention can either be administered systemically, locally, or by way of cell-based therapies (i.e., an agent of the invention can be administered to a patient by administering a cell that expresses that agent to the patient). The cell can be a cell administered to the patient solely for the purpose of expressing the therapeutic agent. The cell can also be a cell of a cellular, tissue, or organ transplant. For example, transplanted cells (e.g., islet cells) or cells within tissues or organs (e.g., cells within a patch of skin or a liver, kidney, or heart) can be treated with an agent or transduced with a nucleic acid molecule that encodes an agent ex vivo (e.g., prior to transplantation). In this way, the transplanted cell produces its own immunosuppressive agents. For example, a cell with a desirable phenotype (e.g., an insulin producing cell) can be modified to include a gene producing one or more of the immunosuppresive factors of the invention. The transplanted cell, tissue, or organ can be treated either prior to or subsequent to transplantation. Methods of administering agents to patients (or to cells or organs in culture) are known and routinely used by those of ordinary skill in the art and are discussed further below.

Agents that Target IL-15 or an IL-15R

The compositions of the invention can include one or more agents that target IL-15 or an IL-15 receptor. As noted above, a single agent can have multiple functional domains. Agents that target IL-15 or an IL-15R include agents that bind to (or otherwise interact with) IL-15, an IL-15R, or the nucleic acids that encode them as well as agents that bind to and subsequently destroy IL-15R-bearing cells, such as activated T cells. Thus, agents useful in achieving immune suppression can contain two functional moieties: a targeting moiety that targets the agent to an IL-15R-bearing cell and a target-cell depleting (e.g., lytic) moiety that leads to the elimination of the IL-15R-bearing cell. In one embodiment, the targeting moiety binds an IL-15R without effectively transducing a signal through that receptor. For example, the targeting moiety can include a mutant IL-15 polypeptide, and the target-cell depleting moiety can include the Fc region of an immunoglobulin molecule. The Fc region can be derived from an IgG, such as human IgG1, IgG2, IgG3, IgG4, or analogous mammalian IgGs or from an IgM, such as human IgM or analogous mammalian IgMs. In a preferred embodiment, the Fc region includes the hinge, CH2 and CH3 domains of human IgG1 or murine IgG2a. Although the invention is not limited to agents that work by any particular mechanism, it is believed that the Fc region mediates complement and phagocyte-driven elimination of IL-15R-bearing cells.

Mutant IL-15 polypeptides that bind the IL-15 receptor complex with an affinity similar to wild-type IL-15, but fail to fully activate signal transduction, have been produced. These mutant polypeptides compete effectively with wild-type IL-15 polypeptides and can inhibit one or more of the events that normally occur in response to IL-15 signaling, such as cellular proliferation. The "wild-type IL-15 polypeptide" referred to herein is a polypeptide that is identical to a naturally occurring IL-15 (e.g., a wild-type IL-15 polypeptide is shown in FIG. 2). In contrast, a "mutant IL-15 polypeptide" is a polypeptide that has at least one mutation relative to wild-type IL-15 and that inhibits at least one of the in vivo or in vitro activities that are usually promoted by wild-type IL-15.

A mutant IL-15 polypeptide that can be used according to the present invention will generally block at least 40%, more preferably at least 70%, and most preferably at least 90% of one or more of the activities of the wild-type IL-15 molecule. The ability of a mutant IL-15 polypeptide to block wild-type IL-15 activity can be assessed by numerous assays, including the BAF-BO3 cell proliferation assay described herein (in which the cells were transfected with a construct encoding IL-2Rβ). Further, mutant polypeptides of the invention can be defined according the particular percent identity they exhibit with wild-type IL-15. When examining the percent identity between two polypeptides, the length of the sequences compared will generally be at least 16 amino acids, preferably at least 20 amino acids, more preferably at least 25 amino acids, and most preferably at least 35 amino acids. The term "identity," as used in reference to polypeptide or DNA sequences, refers to the identity between subunits (amino acid residues of proteins or nucleotides of DNA molecules) within the two polypeptide or DNA sequences being compared. When a subunit position in both of the molecules is occupied by the same monomeric subunit (i.e., the same amino acid residue or nucleotide), then the molecules are identical at that position. The similarity between two amino acid sequences or two nucleotide sequences is a direct function of the number of identical positions. Thus, a polypeptide that is 50% identical to a reference polypeptide that is 100 amino acids long can be a 50 amino acid polypeptide that is completely identical to a 50 amino acid long portion of the reference polypeptide. It might also be a 100 amino acid long polypeptide that is 50% identical to the reference polypeptide over its entire length. Of course, many other polypeptides will meet the same criteria. Identity is typically and most conveniently measured using sequence analysis software, such as the Sequence Analysis Software Package of the Genetics Computer Group at the University of Wisconsin Biotechnology Center (1710 University Avenue, Madison, Wis. 53705), with the default parameters thereof.

A mutant IL-15 polypeptide of the invention can be at least 65%, preferably at least 80%, more preferably at least 90%, and most preferably at least 95% (e.g., 96%, 97%, 98% or 99%) identical to wild-type IL-15. The mutation can consist of a change in the number or content of amino acid residues. For example, the mutant IL-15 can have a greater or a lesser number of amino acid residues than wild-type IL-15. Alternatively, or in addition, the mutant polypeptide can contain a substitution of one or more amino acid residues that are present in the wild-type IL-15. The mutant IL-15 polypeptide can differ from wild-type IL-15 by the addition, deletion, or substitution of a single amino acid residue, for example, an addition, deletion or substitution of the residue at position 156. Similarly, the mutant polypeptide can differ from wild-type by an addition, deletion, or substitution of two amino acid residues, for example, the residues at positions 156 and 149. For example, the mutant IL-15 polypeptide can differ from wild-type IL-15 by the substitution of aspartate for glutamine at residues 156 and 149 (as shown in FIG. 1). Mutant polypeptides useful as targeting agents, like wild-type IL-15, recognize and bind a component of the IL-15R. In one embodiment, the mutation of IL-15 is in the carboxy-terminal domain of the cytokine, which is believed to bind IL-2Rγ (the IL-2 receptor subunit). Alternatively, or in addition, mutant IL-15 polypeptides can include one or more mutations within IL-2Rβ (the IL-2 receptor β subunit) binding domain.

In the event a mutant IL-15 polypeptide contains a substitution of one amino acid residue for another, the substitution can be, but is not necessarily, a conservative substitution, which includes a substitution within the following groups: glycine, alanine; valine, isoleucine, leucine; aspartic acid, glutamic acid; asparagine, glutamine; serine, threonine; lysine, arginine; and phenylalanine, tyrosine.

Instead of using, or in addition to using, an IL-15 targeting polypeptide (e.g., a mutant IL-15 polypeptide), the therapeutic agent can be an antibody. For example, IL-15 can be targeted (i.e., specifically bound) with an antibody. Similarly, the IL-15R can be targeted with antibodies that bind a component of the IL-15R (e.g., the IL-15Rα subunit). The methods by which antibodies, including humanized antibodies, can be generated against a component of the IL-15R are well known in the art. The antibodies preferably should be able to activate complement and phagocytosis, for example, human IgG3 and IgG1 (preferably the latter) subclasses, or murine IgG2a subclass.

The methods of the invention can also be carried out with compositions that contain: (a) two or more agents, each of which promote T cell death or (b) at least one agent that promotes T cell death and at least one agent that inhibits T cell proliferation. The agent that promotes T cell death can do so by promoting passive cell death, which occurs when a T cell is deprived of a factor required for its survival. IL-15 is one such agent (others are described below). Thus, agents that interfere with the ability of IL-15 to serve as a survival factor (e.g., an antibody that specifically binds to IL-15 or the IL-15 receptor) can be included in the compositions of the invention (e.g., a composition can include an agent that promotes AICD, an agent that promotes passive cell death (e.g., an anti-IL-15 antibody), and, optionally, an agent that inhibits T cell proliferation.

As described above, agents useful in achieving immune suppression can contain two functional moieties: a targeting moiety that targets the agent to an IL-15R-bearing cell (such as the mutant IL-15 molecule just described) and a target-cell depleting moiety that, for example, lyses or otherwise leads to the elimination of, the IL-15R-bearing cell. Thus, the agent can be a chimeric polypeptide that includes a mutant IL-15 polypeptide and a heterologous polypeptide such as the Fc region of the IgG and IgM subclasses of antibodies. The Fc region may include a mutation that inhibits complement fixation and Fc receptor binding, or it may be target-cell depleting (i.e., able to destroy cells by binding complement or by another mechanism, such as antibody-dependent complement lysis).

The Fc region can be isolated from a naturally occurring source, recombinantly produced, or synthesized Oust as any polypeptide featured in the present invention can be). For example, an Fc region that is homologous to the IgG C-terminal domain can be produced by digestion of IgG with papain. IgG Fc has a molecular weight of approximately 50 kDa. The polypeptides of the invention can include the entire Fc region, or a smaller portion that retains the ability to lyse cells. In addition, full-length or fragmented Fc regions can be variants of the wild-type molecule. That is, they can contain mutations that may or may not affect the function of the polypeptide.

Reference is made herein to agents that "target" an interleukin or an interleukin receptor. Targeting occurs when an agent directly or indirectly binds to, or otherwise interacts with, an interleukin or an interleukin receptor in a way that affects the activity of the interleukin or the interleukin receptor. Activity can be assessed by those of ordinary skill in the art and with routine laboratory methods. For example, one can assess the strength of signal transduction or another downstream biological event that occurs, or would normally occur, following receptor binding. The activity generated by an agent that targets an interleukin or an interleukin receptor can be, but is not necessarily, different from the activity generated when a naturally occurring interleukin binds a naturally occurring interleukin receptor. For example, an agent that targets an IL-2 receptor falls within the scope of the invention even if that agent generates substantially the same activity that would occur had the receptor been bound by naturally occurring IL-2. When an agent generates activity that is substantially the same as, or greater than, the activity generated by a naturally occurring ligand, the agent can be described as a receptor agonist (the agent and the natural ligand being examined under the same conditions). When an agent generates activity that is less than the activity generated by a naturally occurring ligand, the agent can be described as an antagonist of the receptor (if the agent's primary interaction is with the receptor; e.g., mIL-15) or of the interleukin (if the agent's primary interaction is with the interleukin; e.g., an anti-IL-15 antibody). Here again, levels of activity are assessed by testing the agent and the naturally occurring receptor (or ligand) under the same conditions.

The Fc region that can be part of the agents of the invention can be "target-cell depleting" or "non-target-cell depleting." A non-target-cell depleting Fc region typically lacks a high affinity Fc receptor binding site and a C'1q binding site. The high affinity Fc receptor binding site of murine IgG Fc includes the Leu residue at position 235 of IgG Fc. Thus, the murine Fc receptor binding site can be destroyed by mutating or deleting Leu 235. For example, substitution of Glu for Leu 235 inhibits the ability of the Fc region to bind the high affinity Fc receptor. The murine C'1q binding site can be functionally destroyed by mutating or deleting the Glu 318, Lys 320, and Lys 322 residues of IgG. For example, substitution of Ala residues for Glu 318, Lys 320, and Lys 322 renders IgG1 Fc unable to direct antibody-dependent complement lysis. In contrast, a target-cell depleting IgG Fc region has a high affinity Fc receptor binding site and a C'1q binding site. The high affinity Fc receptor binding site includes the Leu residue at position 235 of IgG Fc, and the C'1q binding site includes the Glu 318, Lys 320, and Lys 322 residues of IgG1. Target-cell depleting IgG Fc has wild-type residues or conservative amino acid substitutions at these sites. Target-cell depleting IgG Fc can target cells for antibody dependent cellular cytotoxicity or complement directed cytolysis (CDC). Appropriate mutations for human IgG are also known (see, e.g., Morrison et al., *The Immunologist* 2:119-124, 1994; and Brekke et al., *The Immunologist* 2:125, 1994).

Agents that target the IL-15R can be mutant IL-15 polypeptides, optionally fused to an antigenic tag (e.g., a FLAG sequence). FLAG sequences are recognized by biotinylated, highly specific, anti-FLAG antibodies, as described herein (see also Blanar et al., *Science* 256:1014, 1992; LeClair et al., *Proc. Natl. Acad. Sci. USA* 89:8145, 1992).

In addition, soluble Il-15R α chain can be used as antagonist. While the IL-15 receptor complex consists of α β γ subunits, the α chain alone displays a high affinity for IL-15. Thus, soluble IL-15R α chain will bind IL-15 and prevent IL-15 from binding to a cell surface-bound IL-15R complex. Thus, a soluble IL-15R α chain can act as a receptor-specific antagonist.

Construction of soluble IL-15R α chain involves cloning the extracellular fragment of the IL-15R α chain from receptor-positive cells, such as activated T cells or receptor expressing cell lines, and, optionally, fusing it to a molecular tag sequence. The tag sequence can be, for example, FLAG, GST, or Histidine. This genetic construct in an expression vector can be transfected into expressing cell lines. The tagged soluble IL-15R α chain produced by expressing cell lines will be purified using mAbs specific for the Tag sequence. Furthermore, an IL-15R extracellular domain can be linked (e.g., fused by way of a peptide bond) to an immunoglobulin Fc domain (e.g. hinge, CH2 and CH3 domains of Immunoglogulin G), preferably of an IgG or IgM subtype. Such a fusion protein could be expressed in a suitable cell type, many of which are known to those of ordinary skill in the art.

Agents that Target IL-2 or an IL-2 Receptor

To inhibit an immune response, the agents that target IL-15R-bearing cells, described above, can be administered with an agent that targets IL-2 or an IL-2R. An agent that is administered "with" another may be, but is not necessarily, administered at the same time or in the same manner (while this comment is stated in the context of a discussion of IL-2-related agents, it is applicable for any of the agents or molecules combined in the compositions of the invention). For example, an agent that targets an IL-15R may be administered before or after an agent that targets an IL-2R. Similarly, an agent that targets IL-15 or an IL15R can be administered ex vivo (to treat, for example, a cell, tissue, or organ that is slated for transplantation) while an agent that targets IL-2 or an IL-2R can be administered systemically (e.g., intravenously) to a patient (e.g. a patient who has received a transplant that was treated ex vivo with an agent that targets IL-15). Similarly, one can administer an agent that promotes AICD at a different time or in a different manner than an agent that inhibits cellular proliferation. Thus, in the methods of the invention, any of the agents or types of molecules that are combined in the compositions of the invention can be administered separately.

To inhibit an IL-2R, one can administer any agent that binds to and antagonizes IL-2 or an IL-2R. Agents that target IL-2 or an IL-2R include agents that bind to IL-2 or an IL-2R as well as agents that bind to and subsequently destroy IL-2R-bearing cells, such as activated T cells. As described above in the context of IL-15 targeting, agents useful in achieving immune suppression can contain a moiety that targets the agent to an IL-2R-bearing cell and a target-cell depleting (e.g., lytic) moiety that leads to the elimination of the IL-2R-bearing cell. For example, the targeting moiety can bind an IL-2R without effectively transducing a signal through that receptor. In the event an Fc region is included, that region can be derived from the same immunoglobulin molecules described above.

Targeting agents, such as an IL-2/Fc agent (e.g., see Zheng et al., *J. Immunol.* 163:4041-4048, 1999) can be administered with an agent that prevents IL-2-mediated IL-2R signaling, such as rapamycin. Agents that inhibit cellular proliferation are well known to those of ordinary skill in the art (and are discussed further below).

Instead of using, or in addition to using, an IL-2R targeting polypeptide (e.g., an IL-2 polypeptide), the therapeutic agent used in combination with an IL-15 antagonist can be an anti-IL-2 or an anti-IL-2R antibody (e.g., a humanized antibody) that antagonizes IL-2 or the IL-2R, respectively.

As explained above, the methods of the invention (e.g., methods of inhibiting an immune response (e.g., a cellular immune response), methods of inhibiting transplant rejection, and methods of treating cancer) can also be carried out with compositions (e.g., pharmaceutically acceptable compositions) that contain: (a) two or more agents, each of which promote T cell death or (b) at least one agent that promotes T cell death and at least one agent that inhibits T cell proliferation. The agent that promotes T cell death can do so by promoting AICD (activation induced cell death), and such agents include IL-2 and molecules that function as IL-2 agonists. For example, IL-2/Fc, mutants of IL-2 that retain the ability to bind and transduce a signal through the IL-2 receptor, and antibodies that specifically bind and agonize the IL-2 receptor (e.g., an antibody that specifically binds the at subunit of the IL-2 receptor) can be included in the compositions of the invention. Other agents that promote AICD include Fas Ligand (FasL), which stimulates T cell death by activating the Fas signal transduction cascade on activated T cells, and biologically active mutants thereof.

Agents that Promote Passive Cell Death

Passive T cell death occurs when a T cell is deprived of an agent that is required for its survival. In addition to IL-15, factors including IL-4, IL-7, OX-40 ligand, IFNβ, 4-1BB and IGF-I are essential (i.e., T cells die in the absence of each of these factors; see, e.g., Tu et al., *J. Immunol.* 165:1331-1336, 2000; Tsuda et al., *J. Immunol. Meth.* 236:37-51, 2000; Bertolino et al., *Int. Immunol.* 11:1225-1238, 1999; Takahashi et al., *J. Immunol.* 162:5037-5040, 1999; Pilling et al., *Eur. J. Immunol.* 29:1041-1050, 1999; Chu et al., *J. Immunol.* 162: 1896-1903, 1999; and Weinberg et al., *Semin. Immunol.* 10:471-480, 1998). One can deprive T cells of one or more of these factors (IL-15, IL-4, IL-7, etc.) by, for example, exposing the cells, in vivo or in culture, to agents that selectively bind to one or more of the factors or otherwise prevent them from interacting with the T cell as they normally would (the result of the deprivation being passive cell death).

Agents that Promote ADCC or CDC

ADCC and CDC can be provoked by agents that bind to the T cell surface and that contain an Fc portion of an immunoglobulin molecule that activates ADCC or CDC. Examples of such agents include antibodies that bind to cell surface structures that are expressed on activated immune cells (e.g., cell surface receptors such as CD154, the IL-2 receptor, and the IL-15 receptor). In addition, one can use a ligand/Fc chimeric fusion protein, which binds to receptor proteins on the surface of activated cells (e.g., an IL-2/Fc or a mIL-15/Fc). Given these examples, other suitable agents will be apparent to those of ordinary skill in the art.

Agents that Inhibit Cellular Proliferation

Agents that inhibit cellular proliferation include rapamycin (Sirolimus), mycophenolate mofetil (MMF), azathioprine, and any other of the agents that are known to be useful for the treatment of hyperproliferative disorders (such as cancer). Well-characterized chemotherapeutics include agents that inhibit nucleic acid metabolism (such as purine and pyrimidine biosynthesis inhibitors, RNA synthesis inhibitors, and DNA binding, DNA modifying, or intercalating agents). These agents are especially useful when the composition used to, for example, inhibit an immune response, also contains an agent such as IL-2/Fc, which not only promotes AICD but also stimulates T cell proliferation.

Agents that inhibit cellular proliferation also include folic acid antimetabolites such as methotrexate (MTX) and pyrimethamine; purine antimetabolites (such as 6-mercaptopurine (6-MP) and azathioprine) and pyrimidine antagonists (such as cytarabine (ara-C), 5-azacytidine, and 5-fluorouracil (these categories were mentioned above); alkylating and other DNA-linking agents (e.g., cyclophosphamide (CPA); mitomycin C, and Doxorubicin (Adriamycin)); vinca alkaloids (e.g., vincristine); and calcineurin inhibitors (e.g., Cyclosporin A, FK506, and Brequinar).

Other agents that can be used to inhibit cellular proliferation include agents that interfere directly with proteins involved in cell cycle regulation (such as anti-CDKs (Cell Division Kinase) or anti-cyclins) or proteins that affect cell proliferation check points (all proliferating cells have check points at different stages of the cell cycle that prevent them from entering the next stage of the cell division cycle (CDC) before they have concluded the previous step). Pathways that feed into check point controls include DNA-, RNA- and protein-synthesis inhibitors (e.g., S6 kinase and PI-3-kinase inhibitors). Cytokinesis inhibitors can also be used.

Procedures for Screening Agents that Inhibit the Immune Response

In addition to testing a candidate agent (e.g., a mutant IL-15 or IL-2 polypeptide) in the in vitro assays described in the examples below, one can use any of the following in vivo assays to test which particular combinations of the agents described herein most effectively bring about immune suppression. For example, one can test one or more of the agents that target the IL-15R in combination with one or more of the agents that antagonize IL-2 or its receptor. These in vivo assays represent only some of the routine ways in which one of ordinary skill in the art could further test the efficacy of agents of the invention. They were selected for inclusion here because of their relevance to the variety of clinical conditions amenable to treatment with agents that target IL-2, IL-15, and their receptors. For example, the assays are relevant to organ transplantation, immune disease, particularly autoimmune disease, graft versus host disease and cancers of the immune system (e.g. cancers that arise when T cells become malignant).

Transplantation Paradigms

To determine whether a combination of agents of the invention achieves immune suppression, the combination can be administered (either directly, by gene-based therapy, or by cell-based therapy) in the context of well-established transplantation paradigms.

Agents of the invention, nucleic acid molecules encoding them (or that hybridize with and thereby inhibit them), can be systemically or locally administered by standard means to any conventional laboratory animal, such as a rat, mouse, rabbit, guinea pig, or dog, before an allogeneic or xenogeneic skin graft, organ transplant, or cell implantation is performed on the animal. Strains of mice such as C57B1-10, B10.BR, and B10.AKM (Jackson Laboratory, Bar Harbor, Me.), which have the same genetic background but are mismatched for the H-2 locus, are well suited for assessing various organ grafts.

Heart Transplantation

A method for performing cardiac grafts by anastomosis of the donor heart to the great vessels in the abdomen of the host was first published by Ono et al. (*J. Thorac. Cardiovasc. Surg.* 57:225, 1969; see also Corry et al., *Transplantation* 16:343, 1973). By way of this surgical procedure, the aorta of a donor heart is anastomosed to the abdominal aorta of the host, and the pulmonary artery of the donor heart is anastomosed to the adjacent vena cava using standard microvascular techniques. Once the heart is grafted in place and warmed to 37° C. with Ringer's lactate solution, normal sinus rhythm will resume. Function of the transplanted heart can be assessed frequently by palpation of ventricular contractions through the abdominal wall. Rejection is defined as the cessation of myocardial contractions. Agents of the invention (e.g., a combination of mutant IL-15/Fc and an antibody that binds to and inhibits IL-2 or IL-2R, or a combination of a mutant IL-15/FC, IL-2/Fc, and rapamycin) would be considered effective in reducing organ rejection if hosts that received these agents experienced a longer period of engraftment of the donor heart than did untreated hosts.

Skin Grafting

The effectiveness of various combinations of the agents of the invention can also be assessed following a skin graft. To perform skin grafts on a rodent, a donor animal is anesthetized and the full thickness skin is removed from a part of the tail. The recipient animal is also anesthetized, and a graft bed is prepared by removing a patch of skin from the shaved flank.

Generally, the patch is approximately 0.5×0.5 cm. The skin from the donor is shaped to fit the graft bed, positioned, covered with gauze, and bandaged. The grafts can be inspected daily beginning on the sixth post-operative day, and are considered rejected when more than half of the transplanted epithelium appears to be non-viable. Agents of the invention (e.g., a combination of mutant IL-15/Fc and an antibody that binds to and inhibits IL-2 or IL-2R, or a combination of a mutant IL-15/FC, IL-2/Fc, and rapamycin) would be considered effective in reducing skin graft rejection if hosts that received these agents experienced a longer period of engraftment of the donor skin than did untreated hosts.

A typical example of a skin grafting experiment, the results of which demonstrate the usefulness of a composition containing IL-2/Fc, mIL-15/Fc and rapamycin, is described in the Examples (below) and summarized in FIG. 12.

Islet Allograft Model

DBA/2J islet cell allografts can be transplanted into rodents, such as 6-8 week-old B6AF1 mice rendered diabetic by a single intraperitoneal injection of streptozotocin (225 mg/kg; Sigma Chemical Co., St. Louis, Mo.). As a control, syngeneic islet cell grafts can be transplanted into diabetic mice. Islet cell transplantation can be performed by following published protocols (for example, see Gotoh et al., *Transplantation* 42:387, 1986). Briefly, donor pancreata are perfused in situ with type IV collagenase (2 mg/ml; Worthington Biochemical Corp., Freehold, N.J.). After a 40-minute digestion period at 37° C., the islets are isolated on a discontinuous Ficoll gradient. Subsequently, 300-400 islets are transplanted under the renal capsule of each recipient. Allograft function can be followed by serial blood glucose measurements (Accu-Check III™; Boehringer, Mannheim, Germany). Primary graft function is defined as a blood glucose level under 11.1 mmol/l on day 3 post-transplantation, and graft rejection is defined as a rise in blood glucose exceeding 16.5 mmol/l (on each of at least 2 successive days) following a period of primary graft function.

Models of Autoimmune Disease

Models of autoimmune disease provide another means to assess combinations of the agents of the invention in vivo. These models are well known to those of ordinary skill in the art and can be used to determine whether a given combination of agents, which includes, for example, an agent that targets an IL-15R, would be therapeutically useful in treating a specific autoimmune disease when delivered either directly, via genetic therapy, or via cell-based therapies.

Autoimmune diseases that have been modeled in animals include rheumatic diseases, such as rheumatoid arthritis and systemic lupus erythematosus (SLE), type I diabetes, and autoimmune diseases of the thyroid, gut, and central nervous system. For example, animal models of SLE include MRL mice, BXSB mice, and NZB mice and their $F_1$ hybrids. These animals can be crossed in order to study particular aspects of the rheumatic disease process; progeny of the NZB strain develop severe lupus glomerulonephritis when crossed with NZW mice (Bielschowsky et al., *Proc. Univ. Otago Med. Sch.* 37:9, 1959; see also *Fundamental Immunology*, Paul, Ed., Raven Press, New York, N.Y., 1989). Similarly, a shift to lethal nephritis is seen in the progeny of NBZ X SWR matings (Data et al., *Nature* 263:412, 1976). The histological appearance of renal lesions in $SNF_1$ mice has been well characterized (Eastcott et al., *J. Immunol.* 131:2232, 1983; see also *Fundamental Immunology*, supra). Therefore, the general health of the animal as well as the histological appearance of renal tissue can be used to determine whether the administration of agents that target an IL-15R and, e.g., target the IL-2R, can effectively suppress the immune response in an animal model of SLE.

One of the MRL strains of mice that develops SLE, MRL-lpr/lpr, also develops a form of arthritis that resembles rheumatoid arthritis in humans (Theofilopoulos et al., *Adv. Immunol.* 37:269, 1985). Alternatively, an experimental arthritis can be induced in rodents by injecting rat type II collagen (2 mg/ml) mixed 1:1 in Freund's complete adjuvant (100 µl total) into the base of the tail. Arthritis develops 2-3 weeks after immunization. The ability of nucleic acid molecules encoding agents of the invention (e.g., agents that target the IL-15R and agents that target the Il-2R or that bind to and inactivate antigen-activated T cells) to suppress an immune response can be assessed by targeting the nucleic acid molecules to T lymphocytes. One way to target T lymphocytes is as follows. Spleen cell suspensions are prepared 2-3 days after the onset of arthritis and incubated with collagen (100 µg/ml) for 48 hours to induce proliferation of collagen-activated T cells. During this time, the cells are transduced with a vector encoding the polypeptide agent of interest. As a control, parallel cultures are grown but not transduced or, transduced with an "empty" vector. The cells are then injected intraperitoneally ($5 \times 10^7$ cells/animal). The effectiveness of the treatment is assessed by following the disease symptoms during the subsequent 2 weeks, as described by Chernajovsky et al. (*Gene Therapy* 2:731-735, 1995). Lesser symptoms, compared to control, indicate that the combined agents of the invention, and the nucleic acid molecules that encode them, function as immunosuppressants and are therefore useful in the treatment of immune disease, particularly autoimmune disease.

The ability of various combinations of agents to suppress the immune response in the case of Type I diabetes can be tested in the BB rat strain, which was developed from a commercial colony of Wistar rats at the Bio-Breeding Laboratories in Ottawa. These rats spontaneously develop autoantibodies against islet cells and insulin, just as occurs with human Type I diabetes. Alternatively, NOD (non-obese diabetic) mice can be used as a model system. A typical example of an experiment in which blood sugar levels are restored in NOD mice following transplantation of allogeneic donor islets is described below and summarized in FIG. 11. The animals were treated with a combination of IL-2/Fc, IL-15/Fc, and rapamycin. The result was long-term engraftment.

Autoimmune diseases of the thyroid have been modeled in the chicken. Obese strain (OS) chickens consistently develop spontaneous autoimmune thyroiditis resembling Hashimoto's disease (Cole et al., *Science* 160:1357, 1968). Approximately 15% of these birds produce autoantibodies to parietal cells of the stomach, just as in the human counterpart of autoimmune thyroiditis. The manifestations of the disease in OS chickens, which could be monitored in the course of any treatment regime, include body size, fat deposit, serum lipids, cold sensitivity, and infertility.

Models of autoimmune disease in the central nervous system (CNS) can also be experimentally induced. An inflammation of the CNS, which leads to paralysis, can be induced by a single injection of brain or spinal cord tissue with adjuvant in many different laboratory animals, including rodents and primates. This model, referred to as experimental allergic encephalomyelitis (EAE) is T cell mediated. Similarly, experimentally induced myasthenia gravis can be produced by a single injection of acetylcholine receptor with adjuvants (Lennon et al., *Ann. N.Y. Acad. Sci.* 274:283, 1976).

Autoimmune diseases of the gut can be modeled in IL-2 or IL-10 "knock out" mice, or in mice that receive enemas containing bovine serum albumin.

Nucleic Acid Molecules that Encode Agents of the Invention

Polypeptide agents of the invention, including those that are fusion proteins (e.g., the mutant IL-15/Fc and IL-2/Fc molecules) can not only be obtained by expression of a nucleic acid molecule in a suitable eukaryotic or prokaryotic expression system in vitro and subsequent purification of the polypeptide agent, but can also be administered to a patient by way of a suitable gene therapeutic expression vector encoding a nucleic acid molecule. Further more a nucleic acid can be introduced into a cell of a graft prior to transplantation of the graft. Thus, nucleic acid molecules encoding the agents described above are within the scope of the invention. Just as polypeptides of the invention can be described in terms of their identity with wild-type polypeptides, the nucleic acid molecules encoding them will necessarily have a certain identity with those that encode the corresponding wild-type polypeptides. For example, the nucleic acid molecule encoding a mutant IL-15 polypeptide can be at least 65%, preferably at least 75%, more preferably at least 85%, and most preferably at least 95% (e.g., 96%, 97%, 98%, or 99%) identical to the nucleic acid encoding wild-type IL-15. For nucleic acids, the length of the sequences compared will generally be at least 50 nucleotides, preferably at least 60 nucleotides, more preferably at least 75 nucleotides, and most preferably 110 nucleotides.

The nucleic acid molecules that encode agents of the invention can contain naturally occurring sequences, or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

The nucleic acid molecules of the invention are referred to as "isolated" because they are separated from either the 5' or the 3' coding sequence with which they are immediately contiguous in the naturally occurring genome of an organism. Thus, the nucleic acid molecules are not limited to sequences that encode polypeptides; some or all of the non-coding sequences that lie upstream or downstream from a coding sequence can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced by in vitro transcription.

The isolated nucleic acid molecules of the invention can include fragments not found as such in the natural state. Thus, the invention encompasses recombinant molecules, such as those in which a nucleic acid sequence (for example, a sequence encoding a mutant IL-15) is incorporated into a vector (for example, a plasmid or viral vector) or into the genome of a heterologous cell (or the genome of a homologous cell, at a position other than the natural chromosomal location).

As described above, agents of the invention can be fusion proteins. In addition to, or in place of, the heterologous polypeptides described above, a nucleic acid molecule encoding an agent of the invention can contain sequences encoding a "marker" or "reporter." Examples of marker or reporter genes include β-lactamase, chloramphenicol acetyltransferase (CAT), adenosine deaminase (ADA), aminoglycoside phosphotransferase ($neo^r$, $G418^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). As with many of the standard procedures associated with the practice of the invention, one of ordinary skill in the art will be aware of additional useful reagents, for example, of additional sequences that can serve the function of a marker or reporter.

The nucleic acid molecules of the invention can be obtained by introducing a mutation into an agent of the invention (e.g., an IL-15 molecule or an IL-2 molecule) obtained from any biological cell, such as the cell of a mammal, or produced by routine cloning methods. Thus, the nucleic acids of the invention can be those of a mouse, rat, guinea pig, cow, sheep, horse, pig, rabbit, monkey, baboon, dog, or cat. Preferably, the nucleic acid molecules will be those of a human.

The nucleic acid molecules described above can be contained within a vector that is capable of directing their expression in, for example, a cell that has been transduced with the vector. Accordingly, in addition to polypeptide agents, expression vectors containing a nucleic acid molecule encoding those agents and cells transfected with those vectors are among the preferred embodiments.

Vectors suitable for use in the present invention include T7-based vectors for use in bacteria (see, e.g., Rosenberg et al., *Gene* 56:125, 1987), the pMSXND expression vector for use in mammalian cells (Lee and Nathans, *J. Biol. Chem.* 263:3521, 1988), yeast expression systems, such as *Pichia pastoris* (for example the PICZ family of expression vectors from Invitrogen, Carlsbad, Calif.) and baculovirus-derived vectors (for example the expression vector pBacPAK9 from Clontech, Palo Alto, Calif.) for use in insect cells. The nucleic acid inserts, which encode the polypeptide of interest in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. One of ordinary skill in the art is well aware of numerous promoters and other regulatory elements that can be used to direct expression of nucleic acids.

In addition to sequences that facilitate transcription of the inserted nucleic acid molecule, vectors can contain origins of replication, and other genes that encode a selectable marker. For example, the neomycin-resistance ($neo^r$) gene imparts G418 resistance to cells in which it is expressed, and thus permits phenotypic selection of the transfected cells. Other feasible selectable marker genes allowing for phenotypic selection of cells include various fluorescent proteins, e.g. green fluorescent protein (GFP) and variants thereof. Those of skill in the art can readily determine whether a given regulatory element or selectable marker is suitable for use in a particular experimental context.

Viral vectors that can be used in the invention include, for example, retroviral, adenoviral, and adeno-associated vectors, herpes virus, simian virus 40 (SV40), and bovine papilloma virus vectors (see, e.g., Gluzman (Ed.), *Eukaryotic Viral Vectors*, CSH Laboratory Press, Cold Spring Harbor, N.Y.).

Prokaryotic or eukaryotic cells that contain a nucleic acid molecule that encodes an agent of the invention and express the protein encoded in that nucleic acid molecule in vitro are also features of the invention. A cell of the invention is a transfected cell, i.e., a cell into which a nucleic acid molecule, for example a nucleic acid molecule encoding a mutant IL-15 polypeptide, has been introduced by means of recombinant DNA techniques. The progeny of such a cell are also considered within the scope of the invention. The precise components of the expression system are not critical. For example, a mutant IL-15 polypeptide can be produced in a prokaryotic host, such as the bacterium *E. coli*, or in a eukaryotic host, such as an insect cell (for example, Sf21 cells), or mammalian cells (e.g., COS cells, CHO cells, 293 cells, NIH 3T3 cells, or HeLa cells). These cells are available from many sources, including the American Type Culture Collection (Manassas, Va.). In selecting an expression system, it matters only that the components are compatible with one another. One of ordinary skill in the art is able to make such a determination. Furthermore, if guidance is required in selecting an expression system, one can consult Ausubel et al. (*Current Protocols in Molecular Biology*, John Wiley and Sons, New York, N.Y., 1993) and Pouwels et al. (*Cloning Vectors: A Laboratory Manual*, 1985 Suppl. 1987).

Eukaryotic cells that contain a nucleic acid molecule that encodes the agent of the invention and express the protein encoded in such nucleic acid molecule in vivo are also features of the invention.

Furthermore, eukaryotic cells of the invention can be cells that are part of a cellular transplant, a tissue or organ transplant. Such transplants can comprise either primary cells taken from a donor organism or cells that were cultured, modified and/or selected in vitro before transplantation to a recipient organism (e.g., eurkaryotic cells lines, including stem cells or progenitor cells). Since, after transplantation into a recipient organism, cellular proliferation may occur, the progeny of such a cell are also considered within the scope of the invention. A cell, being part of a cellular, tissue or organ transplant, can be transfected with a nucleic acid encoding a mutant Il-15 polypeptide and subsequently be transplanted into the recipient organism, where expression of the mutant IL-15 polypeptide occurs. Furthermore, such a cell can contain one or more additional nucleic acid constructs allowing for application of selection procedures, e.g. of specific cell lineages or cell types prior to transplantation into a recipient organism.

The expressed polypeptides can be purified from the expression system using routine biochemical procedures, and can be used as diagnostic tools or as therapeutic agents, as described below.

Agents that Target an IL-15R are Useful in Making Diagnoses

Agents that target an IL-15R can be used to determine whether a patient has a disease (e.g., an immune disease, particularly autoimmune disease) that is amenable to treatment with a combination of the agents described herein. The diagnostic method can be carried out, for example, by obtaining a sample of tissue from a patient suspected of having an immune disease, particularly autoimmune disease or a cancer that is manifest as malignant immune cells and exposing that tissue to an antigenically-tagged polypeptide that targets an IL-15R. The sample may be any biological sample, such as a blood, urine, serum, or plasma sample. In addition, the sample may be a tissue sample (e.g., biopsy tissue), or an effusion obtained from a joint (e.g., synovial fluid), from the abdominal cavity (e.g., ascites fluid), from the chest (e.g., pleural fluid), or from the central nervous system (e.g., cerebral spinal fluid). The sample may also consist of cultured cells that were originally obtained from a patient (e.g., peripheral blood mononuclear cells). The sample can be obtained from a mammal, such as a human patient. If the sample contains cells that are bound by the agent to which they are exposed, it is highly likely that they would be bound by that agent (e.g. an agent that targets an IL-15R) in vivo and could thereby be inhibited from proliferating or destroyed in vivo. The presenting symptoms of candidate patients for such testing and the relevant tissues to be sampled given a particular set of symptoms are well known to one of ordinary skill in the art.

Patients Amenable to Treatment

The compositions of the invention are useful in inhibiting T cells that are involved, or would be involved, in an immune response (e.g., a cellular immune response) to an antigen; in inhibiting other cells involved in the pathogenesis of immunological disorders (e.g., monocytes, macrophages, and other antigen presenting cells such as dendritinc cells, NK cells, and granulocytes); and in destroying hyperproliferating cells (as seen, for example, in tissues involved in immunological disorders such as synovial fibroblasts (which are affected in rheumatoid arthritis) keratinocytes (which are affected in psoriasis), or dermal fibroblases (which are affected in systemic lupus erythematosis). Given these examples, other cell types that can usefully be targeted will be apparent to those of ordinary skill in the art. Hyperproliferative cells may also be cancerous cells (e.g., malignant T cells).

Thus, the compositions of the invention can be used to treat patients who are suffering from an immune disease, particularly autoimmune disease, including but not limited to the following: (1) a rheumatic disease such as rheumatoid arthritis, systemic lupus erythematosus, Sjögren's syndrome, scleroderma, mixed connective tissue disease, dermatomyositis, polymyositis, Reiter's syndrome or Behcet's disease (2) type I or type II diabetes (3) an autoimmune disease of the thyroid, such as Hashimoto's thyroiditis or Graves' Disease (4) an autoimmune disease of the central nervous system, such as multiple sclerosis, myasthenia gravis, or encephalomyelitis (5) a variety of phemphigus, such as phemphigus vulgaris, phemphigus vegetans, phemphigus foliaceus, Senear-Usher syndrome, or Brazilian phemphigus, (6) diseases of the skin such as psoriasis or neurodermitis, and (7) inflammatory bowel disease (e.g., ulcerative colitis or Crohn's Disease). Combinations of the agents of the invention can also be used to treat acquired immune deficiency syndrome (AIDS). Similarly, methods by which these agents are administered can be used to treat a patient who has received a transplant of synthetic or biological material, or a combination of both. Such transplants can be organ, tissue or cell transplants, or synthetic grafts seeded with cells, for example, synthetic vascular grafts seeded with vascular cells. In addition, patients suffering from GVHD or patients who have received a vascular injury would benefit from this method.

Because the invention encompasses administration of a target-cell depleting form of an agent that targets the IL-15R (or an IL-2 receptor, or a combination of IL-15 or the IL-15R and IL-2 or the IL-2R), it is possible to selectively kill autoreactive or "transplant destructive" immune cells without massive destruction of normal T cells. Accordingly, the invention features a method of killing cells that express the IL-15R in vivo, which includes activated or autoreactive or "transplant destructive" immune cells or malignant cells. These methods can be carried out by administering to a patient a combination of agents that includes an agent that targets the IL-15R and that activates the complement system, lyses cells by the ADCC mechanism, or otherwise kills cells expressing the wild-type IL-15 receptor complex. This method can be used to treat patients who have IL-15R+ leukemia, lymphoma, or other IL-15R+ malignant diseases, such as colon cancer.

Formulations for Use and Routes of Administration

The methods of the present invention and the therapeutic compositions used to carry them out contain "substantially pure" agents. For example, in the event the agent is a polypeptide, the polypeptide is at least 60% by weight (dry weight) the polypeptide of interest, e.g., a polypeptide that binds and destroys IL-15R-bearing cells. Preferably, the agents (e.g., the polypeptides) are at least 75%, more preferably at least 90%, and most preferably at least 99%, by weight, the agent of interest. Purity can be measured by any appropriate standard method, e.g., column chromatography, polyacrylamide gel electrophoresis, or HPLC analysis.

Although agents useful in the methods of the present invention can be obtained from naturally occurring sources, they can also be synthesized or otherwise manufactured (e.g., agents that bind and destroy IL-15R-bearing cells can be produced by expression of a recombinant nucleic acid molecule). Polypeptides that are derived from eukaryotic organisms or synthesized in E. coli, or other prokaryotes, and polypeptides that are chemically synthesized will be substantially free from their naturally associated components. In the event the polypeptide is a chimera, it can be encoded by a hybrid nucleic acid molecule containing one sequence that encodes all or part of the agent (e.g., a sequence encoding a mutant IL-15 polypeptide and sequence encoding an Fc region of IgG). Agents of the invention (e.g., polypeptides) can be fused to a hexa-histidine tag to facilitate purification of bacterially expressed protein, or to a hemagglutinin tag to facilitate purification of protein expressed in eukaryotic cells.

The techniques that are required to make the agents of the invention are routine in the art, and can be performed without resort to undue experimentation by one of ordinary skill in the art. For example, a mutation that consists of a substitution of one or more of the amino acid residues in IL-15 can be created using the PCR-assisted mutagenesis technique described herein for the creation of the mutant IL-15 polypeptide in which glutamine residues at positions 149 and 156 were changed to aspartic acid residues. Mutations that consist of deletions or additions of amino acid residues (to an IL-15 polypeptide or to any of the other useful polypeptides described herein, e.g., polypeptides that inhibit costimulation or that bind activated T cells) can also be made with standard recombinant techniques. In therapeutic applications, agents of the invention can be administered with a physiologically acceptable carrier, such as physiological saline. The therapeutic compositions of the invention can also contain a carrier or excipient, many of which are known to one of ordinary skill in the art. Excipients that can be used include buffers (e.g., citrate buffer, phosphate buffer, acetate buffer, and bicarbonate buffer), amino acids, urea, alcohols, ascorbic acid, phospholipids, proteins (e.g., serum albumin), EDTA, sodium chloride, liposomes, mannitol, sorbitol, and glycerol. The agents of the invention can be formulated in various ways, according to the corresponding route of administration. For example, liquid solutions can be made for ingestion or injection; gels or powders can be made for ingestion, inhalation, or topical application. Methods for making such formulations are well known and can be found in, for example, "Remington's Pharmaceutical Sciences."

Routes of administration are also well known to skilled pharmacologists and physicians and include intraperitoneal, intramuscular, subcutaneous, and intravenous administration. Additional routes include intracranial (e.g., intracisternal or intraventricular), intraorbital, opthalmic, intracapsular, intraspinal, intraperitoneal, transmucosal, topical, subcutaneous, and oral administration. It is expected that the intravenous or intra-arterial routes will be preferred for the administration of agents that target an IL-15 receptor. The subcutaneous route may also be used frequently as the subcutaneous tissue provides a stable environment for polypeptides, from which they can be slowly released.

In case of cell-based therapies (gene therapies), the cells/tissues/organs could either be transfected by incubation, infusion or perfusion prior to transplantation with a nucleic acid composition, such that the therapeutic protein is expressed and subsequently released by the transplanted cells/tissues/organs within the recipient organism. As well, the cells/tissues/organs could undergo a pretreatment by perfusion or simple incubation with the therapeutic protein prior to transplantation in order to eliminate transplant-associated immune cells adherent to the donor cells/tissues/organs (although this is only a side aspect, which will probably not be of any clinical relevance). In the case of cell transplants, the cells may be administered either by an implantation procedure or with a catheter-mediated injection procedure through the blood vessel wall. In some cases, the cells may be administered by release into the vasculature, from which the subsequently are distributed by the blood stream and/or migrate into the surrounding tissue (this is done in islet cells transplantation, where the islet cells are released into the portal vein and subsequently migrate into liver tissue).

It is well known in the medical arts that dosages for any one patient depend on many factors, including the general health, sex, weight, body surface area, and age of the patient, as well as the particular compound to be administered, the time and route of administration, and other drugs being administered concurrently. Dosages for the polypeptide of the invention will vary, but can, when administered intravenously, be given in doses on the order of magnitude of 1 microgram to 10 mg/kg body weight or on the order of magnitude of 0.01 mg/l to 100 mg/l of blood volume. A dosage can be administered one or more times per day, if necessary, and treatment can be continued for prolonged periods of time. Determining the correct dosage for a given application is well within the abilities of one of ordinary skill in the art.

EXAMPLES

Reagents

The following reagents were used in the studies described herein: recombinant human IL-2 was obtained from Hoffman-La Roche (Nutley, N.J.); rapamycin was obtained from Wyeth-Ayerst (Princeton, N.J.); cyclosporine-A (CsA) was obtained from Sandoz (East Hanover, N.J.); RPMI-1640 and fetal calf serum (FCS) were obtained from BioWittaker (Walkersville, Md.); penicillin, streptomycin, G418, and strepavidin-RED670 were obtained from Gibco-BRL (Gaithersburg, Md.); dexamethasone, PHA, lysozyme, Nonidet P-40, NaCl, HEPES, and PMSF were obtained from Sigma (St. Louis, Mo.); Ficoll-Hypaque was obtained from Pharmacia Biotech (Uppsala, Sweden); recombinant human IL-15 and anti-human IL-15 Ab were obtained from PeproTech (Rocky Hill, N.J.); anti-FLAG Ab and anti-FLAG-affinity beads were obtained from International Biotechnologies, Inc. (Kodak, New Haven, Conn.); pRcCMV was obtained from InVitrogen Corporation (San Diego, Calif.); genistein was obtained from ICN Biomedicals (Irvine, Calif.); disuccinimidyl suberate (DSS) was obtained from Pierce (Rockford, Ill.); restriction endonucleases were obtained from New England Biolabs (Beverly, Mass.); [$^3$H]TdR was obtained from New England Nuclear (Boston, Mass.); and fluorescent dye conjugated antibodies CD25-PE[3], CD14-PE, CD16-PE, CD122-PE, CD4-FITC, CD8-FITC, IgG1-PE or IgG1-FITC were obtained from Beckton/Dickinson (San Jose, Calif.). FLAG peptide was synthesized in the Peptide Synthesis Facility at Harvard Medical School.

Production of FLAG-HMK-IL-15 Fusion Protein

To study the cellular pattern of human IL-15 receptor expression, a plasmid that could be used to express an IL-15 fusion protein was constructed. The plasmid encodes an IL-15 polypeptide having an N-terminus covalently bound to the 18 amino acid FLAG-HMK-sequence (FLAG-HMK-IL-15). FLAG sequences are recognized by biotinylated, highly specific anti-FLAG antibodies (Blanar et al., *Science* 256: 1014, 1992); LeClair et al., *Proc. Natl. Acad. Sci. USA* 89:8145, 1992) while HMK (Heart Muscle Kinase recognition site) sequences allow introduction of radioactive label [$^{32}$P] into the molecule (Blanar et al., supra, LeClair et al., supra).

For the construction of the plasmid FLAG-HMK-IL-15, a 322 bp cDNA fragment encoding mature IL-15 protein was amplified by PCR utilizing synthetic oligonucleotides: sense 5'-GGAATTCAACTGGGTGAATGTAATA-3' (SEQ ID NO:5; EcoRI site (underlined) plus bases 145-162); antisense 5'-CGGGATCCTCAAGAAGTGTTGATGAA-3' (SEQ ID NO:6; BamHI site [underlined] plus bases 472-489). The template DNA was obtained from PHA-activated human PBMCs. The PCR product was purified, digested with EcoRI and BamHI, and cloned into the pAR(DRI)59/60 plasmid digested with EcoRI-BamHI as described (Blanar et al., *Science* 256:1014, 1992; LeClair et al., *Proc. Natl. Acad. Sci. USA* 89:8145, 1992). The backbone of the pAR(DRI)59/60 plasmid contains in frame sequences encoding the FLAG and HMK recognition peptide sequences (Blanar et al, *Science* 256:1014, 1992; LeClair et al., *Proc. Natl. Acad. Sci. USA* 89:8145, 1992).

Expression and Purification of FLAG-HMK-IL-15 Fusion Protein

The IL-15-related fusion construct, FLAG-HMK-IL-15, was expressed in BL-21 strain *E. coli* and affinity purified with anti-FLAG coated beads as described (Blanar et al., *Science* 256:1014, 1992; LeClair et al., *Proc. Natl. Acad. Sci. USA* 89:8145, 1992). The fusion protein was eluted from affinity columns after extensive washing with 0.1 M glycine (pH 3.0). The eluate containing FLAG-HMK-IL-15 was dialyzed against a buffer containing 50 mM Tris (pH 7.4) and 0.1 M NaCl for 18 hours at 4° C., filtered through a 0.2 µm membrane, and stored at −20° C.

FLAG-HMK-IL-15 Binds the IL-15Rα Subunit

The purified FLAG-HMK-IL-15 fusion protein was tested to determine whether it interacts with cell surface IL-15 receptors. As described above, [$^{32}$P]-FLAG-HMK-IL-15 was added to cultures of PBMCs that were activated by a mitogen, PHA. In order to permanently bind interactive proteins to one another, the chemical cross-linker disuccinimidyl suberate (DSS) was added. The cells were washed, lysed, centrifuged, and detergent-soluble proteins were separated by SDS-PAGE. Autoradiography of SDS-PAGE separated proteins revealed a single 75-80 kDa band corresponding to the combined molecular weight of FLAG-HMK-IL-15 (15 kDa) and the human IL-15Rα subunit (60-65 kDa). The identity of this band as the IL-15Rα subunit was confirmed by cross-linking experiments conducted in the presence of a molar excess of hIL-15. Under these conditions, we failed to detect the radio labeled 15 kDa band. Thus, the conformation of [$^{32}$P]-FLAG-HMK-IL-15 fusion proteins allows site specific binding to the 60-65 kDa IL-15Rα subunit expressed on the surface of mitogen-activated PBMCs.

FLAG-HMK-IL-15 is a Biologically Active Growth Factor that Requires Expression of IL-2Rβ

In the next series of experiments, the FLAG-HMK-IL-15 fusion protein was tested to determine whether it could function as a biologically active growth factor. PHA-activated human PBMCs proliferate in response to either FLAG-HMK-IL-15 or human recombinant IL-2, as detected via the [$^3$H]-TdR incorporation assay. A FLAG peptide lacking the IL-15 sequence does not stimulate cell proliferation. As does IL-2, the FLAG-HMK-IL-15 fusion protein stimulates proliferation of IL-2Rγ⁺BAF-BO3 cell transfectants that express the IL-2Rβ subunit. The FLAG-HMK-IL-15 fusion protein does not, however, stimulate the proliferation of parental BAF-BO3 cells that were transfected with a vector lacking IL-2Rβ chain sequences. Thus, FLAG-HMK-IL-15 is a biologically active growth factor that requires expression of IL-2Rβ chains upon target cells in order to stimulate cellular proliferation.

Mitogen-Activated, But Not Resting, PBMCs Express the IL-15Rα Subunit

The FLAG-HMK-IL-15 fusion protein, biotinylated anti-FLAG antibody, and streptavidin-RED670 were employed to detect expression of IL-15 binding sites on human PBMCs by cytofluorometric analysis. The PBMCs tested were either freshly isolated or PHA-activated. These cells were washed and incubated with either medium alone or FLAG-HMK-IL-15 followed by anti-FLAG biotinylated Ab and streptavidin-RED670. The stained cells were analyzed by flow cytometry. PBMCs that were activated with PHA expressed IL-15Rα proteins but resting PBMCs did not. In keeping with the result of the cross-linking experiments described above, binding of FLAG-HMK-IL-15 to PHA activated PBMCs is blocked by a molar excess of rIL-15, thereby demonstrating the specificity of FLAG-HMK-IL-15 binding for IL-15 binding sites. Both activated CD4⁺ and CD8⁺ cells express IL-15α chains. Activation induced IL-15Rα chains were also detected on CD14⁺ (monocyte/macrophage) cells and CD16⁺ (natural killer) cells.

IL-2Rα and IL-2Rβ Subunits are Not Required for IL-15 Binding

FACS analysis of PHA-activated PBMCs stained with FLAG-HMK-IL-15 proteins and anti-CD25 Mab, against the IL-2Rα subunit, reveals cell populations expressing both IL-15Rα and IL-2Rα subunits, as well as cell populations that express either subunit, but not both. There are IL-2Rα⁺ cells that do not bind FLAG-HMK-IL-15. Almost all PBMCs that were stimulated with PHA for only one day express either IL-15Rα or IL-2Rβ chains, but not both proteins. In contrast, 3 days following PHA stimulation, a far larger population of IL-15Rα⁺, IL-2Rβ⁺ cells (double positive) and a far smaller population of IL-15Rα⁺, IL-2Rβ⁻ cells (single positive) were noted. Interestingly, there are IL-2Rβ⁺ cells that fail to bind IL-15. Therefore, expression of IL-2Rβ chains is not sufficient for IL-15 binding.

Taken together, these data indicate that IL-15 can bind IL-15Rα⁺, IL-2Rα⁻, and IL-2Rα⁻ cells. A similar conclusion was reached through experimentation that probed the interaction of IL-15 with IL-2Rα⁻, β⁻ cells transfected with IL-15Rα subunit (Anderson et al., *J. Biol. Chem.* 270:29862, 1995; Giri et al., *EMBO J.* 14:3654, 1995). In addition to the requirement for IL-15Rα subunit expression, the IL-2Rβ and IL-2Rγ subunits are required to render cells sensitive to IL-15 triggered growth.

In summary, the experiments presented above have demonstrated that: (i) IL-15Rα subunits are rapidly expressed by activated macrophages, T cells, and NK cells, and (ii) induction of the IL-15Rα subunit is blocked by dexamethasone but not by CsA or rapamycin. In addition, the experiments have confirmed that the IL-15Rα subunit is necessary and sufficient for IL-15 binding and that the FLAG-HMK-IL-15 fusion protein is an extremely useful tool for studying IL-15 receptors.

The IL-2Rβ Subunit is Critical for Both IL-2 and IL-15 Signal Transduction

Decreasing the viability of activated T cells and thereby depleting activated T cells provides a way to decrease the production of lymphokines and mitogens that contribute to accelerated atherosclerosis, allograft rejection, certain leukemias and other immune-mediated pathologies. In addition, blocking the signal transduction pathway activated by IL-15 also provides a way to decrease the production of lymphokines and mitogens that contribute to accelerated atherosclerosis, allograft rejection, certain leukemias and other immune-mediated pathologies. When activated, T cells proliferate and express receptors on their cell surface for interleukins. In addition, activated T cells release at least 3 lymphokines: gamma interferon, B cell differentiation factor II, and IL-3. These lymphokines can produce various undesirable events, such as allograft rejection. In contrast, resting T cells and long-term memory T cells do not express lymphokine receptors. This difference in receptor expression provides a means to target activated immune cells without interfering with resting cells. Molecules designed to recognize some subunit of the IL-15R will recognize activated monocytes/macrophages as well as activated T cells and can be used to selectively inhibit or destroy these cells. Derivatives of IL-15 that bind to an IL-15R subunit but that lack IL-15 activity, either because they block the binding and/or uptake of bona fide IL-15, are useful in the method of the invention. The mutant IL-15 molecule described below provides a working example of such a derivative.

A Mutant IL-15 Polypeptide that Targets an IL-15R

Genetic Construction of Mutant IL-15

The human IL-15 protein bearing a double mutation (Q149D; Q156D) was designed to target the putative sites critical for binding to the IL-2Rγ subunit. The polar, but uncharged glutamine residues at positions 149 and 156 were mutated into acidic residues of aspartic acid utilizing PCR-assisted mutagenesis. A cDNA encoding the double mutant of IL-15 was amplified by PCR utilizing a synthetic sense oligonucleotide [5'-G GAATTCAACTGGGTGAATGTAATA-3' (SEQ ID NO:5); EcoRI site (underlined hexamer) plus bases 145-162] and a synthetic antisense oligonucleotide (5'-CG GGATCCTCAAGAAGTGTTGATGAACATGT CGACAAT-ATGTACAAAACTGTCCAAAAAT-3'(SEQ ID NO:7); BamHI site (underlined hexamer) plus bases 438-489; mutated bases are singly underlined]. The template was a plasmid containing cDNA that encodes human FLAG-HMK-IL-15. The amplified fragment was digested with EcoRI/BamHI and cloned into the pAR(DRI)59/60 plasmid digested with EcoRI/BamRI as described (LeClair et al., Proc. Natl. Acad. Sci. USA 89:8145, 1989). The presence of a mutation at residue 156 was confirmed by digestion with SalI; the mutation introduces a new SalI restriction site. In addition, mutations were verified by DNA sequencing, according to standard techniques. The FLAG-HMK-IL-15 (Q149D; Q156D) double mutant protein was produced, purified, and verified by sequencing as described above for the FLAG-HMK-IL-15 wild-type protein.

Using this same strategy, mutants that contain a single amino acid substitution, either at position 149 or at position 156 were prepared. As described above, these positions (149 and 156) correspond to positions 101 and 108, respectively, in the mature IL-15 polypeptide, which lacks a 48-amino acid signal sequence.

Similarly, this strategy can be used to incorporate any other amino acid in place of the glutamine residues at positions 149 or 156 or to introduce amino acid substitutions at positions other than 149 and/or 156.

Proliferation of BAF-BO3 Cells in the Presence of IL-15 Related Proteins

The double mutant IL-15 polypeptide may inhibit BAF-BO3 proliferation in a dose-dependent manner: addition of 30 μl (approximately 50 μg/ml) of the double mutant IL-15 inhibited proliferation more completely than did addition of 20 μL of the same concentration of the double mutant IL-15.

Proliferation of PHA-Stimulated Human PBMCs

The ability of the FLAG-HMK-IL-15 double mutant polypeptide to bind PHA activated human PBMCs was demonstrated as follows. PHA-activated PBMCs were washed and incubated with medium alone, or with the FLAG-HMK-IL-15 double mutant. The cells were then incubated with an anti-FLAG biotinylated antibody and stained with streptavidin conjugated to RED670. The stained cells were analyzed by flow cytometry.

FACS Analysis of Leukemic Cell Lines Stained with Wild-Type FLAG-HMK-IL-15

In a series of experiments similar to those above, the ability of the wild-type FLAG-HMK-IL-15 polypeptide to bind leukemia cells was shown. The cells treated were obtained from the leukemic cell lines MOLT-14, YT, HuT-102, and from cell lines currently being established at Beth Israel Hospital (Boston, Mass.), and named 2A and 2B. The cultured cells were washed and incubated with either medium alone or with medium containing the FLAG-HMK-IL-15 wild-type polypeptide. The cells were then incubated with the biotinylated anti-FLAG antibody and stained with RED670-conjugated streptavidin. The stained cells were analyzed by flow cytometry.

Genetic Construction of Additional Mutant IL-15 Chimeric Polyopeptides

In addition to the FLAG-HMK-IL-15 chimera, which provides the mutant IL-15 with an antigenic tag, numerous other polypeptides can be linked to any mutant of IL-15 or IL-2. For example, mutant IL-15 or IL-2 can be linked to the Fc fragment of the IgG subclass of antibodies according to the following method.

Genetic Construction of Mutant IL-15/Fc cDNA for Fcγ2a can be generated from mRNA extracted from an IgG2a secreting hybridoma using standard techniques with reverse transcriptase (MMLV-RT; Gibco-BRL, Grand Island, N.Y.) and a synthetic oligo-dT (12-18) oligonucleotide (Gibco BRL). The mutant IL-15 cDNA can be amplified from a plasmid template by PCR using IL-15 specific synthetic oligonucleotides.

The 5' oligonucleotide is designed to insert a unique NotI restriction site 40 nucleotides 5' to the translational start codon, while the 3' oligonucleotide eliminates the termination codon and modifies the C-terminal Ser residue codon usage from AGC to TCG to accommodate the creation of a unique BamHI site at the mutant IL-15/Fc junction. Synthetic oligonucleotides used for the amplification of the Fcγ2a domain cDNA change the first codon of the hinge from Glu to Asp in order to create a unique BamHI site spanning the first codon of the hinge and introduce a unique XbaI site 3' to the termination codon.

The Fc fragment can be modified so that it is non-target-cell depleting, i.e., not able to activate the complement system. To make the non-target-cell depleting mutant IL-15 construct (mIL-15/Fc), oligonucleotide site directed mutagenesis is used to replace the C'1q binding motif Glu318, Lys320, Lys322 with Ala residues. Similarly, Leu235 is replaced with Glu to inactivate the FcγR I binding site. Ligation of cytokine and Fc" components in the correct translational reading frame at the unique BamHI site yields a 1,236 basepair open reading frame encoding a single 411 amino acid polypeptide (including the 18 amino acid IL-15 signal peptide) with a total of 13 cysteine residues. The mature secreted homodimeric IL-15/ Fc is predicted to have a total of up to eight intramolecular and three inter-heavy chain disulfide linkages and a molecular weight of approximately 85 kDa, exclusive of glycosylation.

Expression and Purification of mIL-15 Receptor Fc Fusion Proteins

Proper genetic construction of mIL-15/Fc can be confirmed by DNA sequence analysis following cloning of the fusion gene as a NotI-XbaI cassette into the eukaryotic expression plasmid pRc/CMV (Invitrogen, San Diego, Calif.). This plasmid carries a CMV promoter/enhancer, a bovine growth hormone polyadenylation signal and a neomycin resistance gene for selection with G418. Plasmids carrying the mIL-15/Fc fusion gene is transfected into Chinese hamster ovary cells (CHO-K1, available from the American Type Culture Collection) by electroporation (1.5 kV/3 μF/0.4 cm/PBS) and selected in serum-free Ultra-CHO media (Bio-Whittaker Inc., Walkerville, Md.) containing 1.5 mg/ml of G418 (Geneticin, Gibco BRL). After subcloning, clones that produce high levels of the fusion protein are selected by screening supernatants from IL-15 by ELISA (PharMingen, San Diego, Calif.). mIL-15/Fc fusion proteins are purified from culture supernatants by protein A sepharose affinity chromatography followed by dialysis against PBS and 0.22 μm filter sterilization. Purified proteins can be stored at $-20°$ C. before use.

Western blot analysis following SDS-PAGE under reducing (with DTT) and non-reducing (without DTT) conditions can be performed using monoclonal or polyclonal anti-mIL-15 or anti Fcγ primary antibodies to evaluate the size and isotype specificity of the fusion proteins. The functional activity of mutant IL-15/Fc can be assessed by a standard T cell proliferation assay, as described above. The following mAbs were obtained from PharMingen (San Diego, Calif.): PE-anti-mouse CD25 (IL-2R α chain, IgG1, PC61), rat anti-mouse CD122 (IL-2R β chain, IgG2b, TM-b1), rat anti-mouse CD132 (IL-2R γc, IgG2b, TUGm2), hamster anti-mouse CD3 (IgG, 145-2C11), hamster anti-mouse CD28 (IgG, 37.51), PE-anti-mouse CD62L (IgG2a, MEL14), PE conjugated hamster anti-mouse Bcl-2 (IgG, 3F11), PE conjugated anti-mouse IL-2 (IgG2b, JES6-5H4), PE-annexin V, biotinylated anti-rat IgG2b, PE-streptoavidin, PE-Cy-Chrome, and PE conjugated isotype control mAbs. A biotinylated mouse anti-FLAG mAb and a rat IgG1 control mAb were obtained from Sigma Chemical Co. (St Louis, Mo.). A B-cell hybridoma secreting rat anti-mouse CD25 mAb (TIB 222, IgG1) was obtained from the American Type Culture Collection (ATCC; Manassas, Va.). Cells were grown in serum free UltraCulture medium (BioWhittaker, Walkerville, Md.) and the mAb in the culture supernatant was purified with a protein G column.

Expression Studies of IL-2 and IL-15 in Vivo.

Recombinant human IL-2 and IL-15 were purchased from R & D System (Minneapolis, Minn.). IL-15-FLAG and IL-15 mutant/Fc fusion proteins were constructed, expressed, and tested as previously reported (Chae et al., *J. Immunol.* 157: 2813-2819, 1996; Kim et al., *J. Immunol.* 161:5742-5748, 1998). Rat anti-mouse γc mAbs (4G3/3E12, IgG2b) were used as previously reported (Li et al. *J. Immunol.* 164:1193-1199, 2000).

Lymphocytes were labeled with fluorochrome 5-carboxy-fluorescein diacetate succinimidyl ester (CFSE; Molecular Probes, Inc., Portland, Oreg.) as follows. Spleens and peripheral lymph nodes were harvested from donor mice and single cell suspensions were prepared in Hanks balanced salt solution (HBSS). Red blood cells were lysed by hypotonic shock. Cells were resuspended in HBSS at $1 \times 10^7$/ml and labeled with CFSE as described by Wells et al. (*J. Clin. Invest.* 100: 3173-3183, 1997).

To activate CFSE-labeled T cells in vivo, DBA/2 mice were irradiated (1000 rad) with a Gammacell Exactor (Kanata, Ontario, Canada). Each mouse then received 4 to $6 \times 10^7$ CFSE-labeled cells in 0.5 ml HBSS via the tail vein. Three days later, the host mice were sacrificed and spleens and peripheral lymph nodes were harvested separately. Single cell suspensions were prepared for cell surface staining and FACS analysis.

In some experiments, irradiated host mice were treated with anti-CD25 mAb or anti-γc mAbs (i.p. at 1 mg/day for 3 days starting at i.v. injection of CFSE-labeled cells). Cell division in vivo was determined on the third day following injection of CFSE-labeled cells. Treatment with IL-15 mutant /Fc fusion protein consisted of 1.5 μg i.p. daily, for three days, starting at i.v. injection of labeled cells.

CFSE-labeled cells activated in vivo in irradiated allogeneic hosts were stained for the expression of IL-2 and IL-15 receptor subunits. To detect IL-2 receptor α chain expression, cells ($2 \times 10^6$) were stained with PE-anti-mouse CD25 mAb on ice for 30 minutes, washed, and resuspended in 1 ml PBS containing 0.5% BSA. To detect IL-2R β and γc expression, cells were incubated with a rat anti-mouse β chain (IgG2b) or βc mAb (IgG2b) on ice for 30 minutes, followed by incubation with a biotinylated anti-rat IgG2b. Cells were washed and further stained with PE-streptoavidin for 20 minutes. Cells were washed and resuspended in PBS-0.5% BSA for analysis. To detect IL-15R α chain expression, cells were incubated with an IL-15-FLAG fusion protein that binds to the α chain (Chae et al., *J. Immunol.* 157:2813-2819, 1996) and then stained with biotinylated mouse anti-FLAG mAb. The cells were then washed and stained with PE-streptoavidin. Isotype matched control mAbs were included in each experiment as a control. All samples were analyzed using FACSort with CellQuest™ software (Becton Dickinson, Mountain View, Calif.). Data were collected and analyzed by gating onto CFSE$^+$ cells. All dividing CFSE$^+$ cells were T cells, as defined by the expression of CD3. At least 100,000 events were collected for each sample.

Apoptosis of dividing T cells in vivo was analyzed as follows. CFSE-labeled lymphocytes were stimulated in vivo in irradiated allogeneic hosts as described above. Cells were harvested from the host spleen or peripheral lymph nodes three days later and stained with PE conjugated annexin V on ice for 15 minutes in labeling buffer. Cell division was identified based on the cells' CFSE profile, and apoptotic cell death in each distinct cell division was analyzed by annexin V staining.

Cells were also stained for intracellular IL-2 and Bcl-2 cytokine expression. CFSE-labeled cells that had been activated in vivo for three days were harvested from the host spleen and lymph nodes. Cells were restimulated in vitro with PMA (50 ng/ml) and ionomycin (500 ng/ml) for four hours and GolgiStop™ (PharMingen) was added for the last two hours of culture. Cells were fixed and permeablized with Cytofix/Cytoperm (PharMingen) at 4° C. for 10 minutes, and then stained with PE-conjugated anti-mouse IL-2 mAb, isotype matched control mAb was included as a control. For Bcl-2 staining, cells were fixed and permeablized with Cytofix/Cytoperm for 10 minutes and stained with PE-conjugated anti-Bcl-2 mAb or isotype control Ab for 30 minutes. Cells were washed and analyzed by FACS.

Cell sorting and in vitro re-stimulation was carried out as follows. CFSE-labeled cells were prepared from irradiated allogeneic hosts three days after i.v. injection of labeled cells. Cell proliferation in vivo was identified through analysis of their CFSE profiles. The second cell divisions were selected, gated, and sorted with FACS Vantage™ sorter (Becton Dickinson) at 2000 events/second. The sorted cells were resuspended in RPMI 1640 medium supplemented with 10% FCS and 1% penicillin and streptomycin at $5 \times 10^5$/ml and plated on anti-CD3 (2 µg/ml) coated plates along with anti-CD28 mAb (1 µg/ml). Three days later, cells were harvested and stained with PE-conjugated anti-mouse CD25 and isotype control Ab. Cell proliferation and IL-2 receptor α chain expression were analyzed by FACS.

Cell sorting and in vitro proliferation assays were carried out as follows. CFSE-labeled cells were prepared from irradiated allogeneic hosts three days after intravenous injection of labeled cells, and cell proliferation in vivo was identified by analysis of the cells' CFSE profile. The second cell division was selected, gated, and sorted with FACS Vantage™. Cells ($1 \times 10^4$/ml) were resuspended in RPMI 1640 medium with 10% FCS and 1% penicillin and streptomycin, and stimulated with IL-2 (40 µ/ml to 500 µ/ml) or IL-15 (5 ng/ml) for 48 hours. Cells were pulsed with 1 mCi $^3$H-TdR (Amersham, Boston, Mass.) for 16 hours and $^3$H-TdR uptake was determined by scintillation counting (Beckman Instrument, Columbia, Md.).

The reagents and techniques described above provided the basis for several findings. First, CFSE-labeled B6AF1 (H-2b/d.k) allogeneic lymphocytes, in contrast to syngeneic controls (Li et al., *Nature Medicine* 5:1298-1302, 1999), proliferated vigorously in irradiated DBA/2 (H-2d) hosts. Approximately 20% of the CFSE-labeled T cells recovered from the host spleen entered the cell cycle within three days of adoptive transfer, and seven to eight discrete rounds of cell division were clearly identified (FIG. 3A). Surprisingly, the IL-2 receptor α chain, which is required for high affinity IL-2 receptor signaling, could not be detected during the first 5 divisions, i.e., this receptor subunit is expressed only after five cell divisions. In contrast, β subunits of the IL-2 receptor were expressed constitutively by all dividing T cells, and their level of expression was increased progressively as cells continued to divide. The pattern of γc expression in vivo differed strikingly from that of the α chain and the β chain (FIG. 3A). Undivided T cells (0 division) expressed very low levels of γ chain (<10%). Following entry into the cell cycle, γ chain was highly expressed by dividing T cells, and the levels of expression continued to increase after each consecutive cell division. After five cell divisions, however, γ chain expression was drastically down regulated, nearly reaching the basal level after the sixth cell division (FIG. 3A).

The differential expression of IL-2 receptor subunits is not due to selective accumulation of a subset of activated T cells in the host spleen, as CFSE-labeled cells harvested from peripheral lymph nodes displayed a remarkably similar pattern of expression for the three subunits of the IL-2 receptor.

Figure 3B:
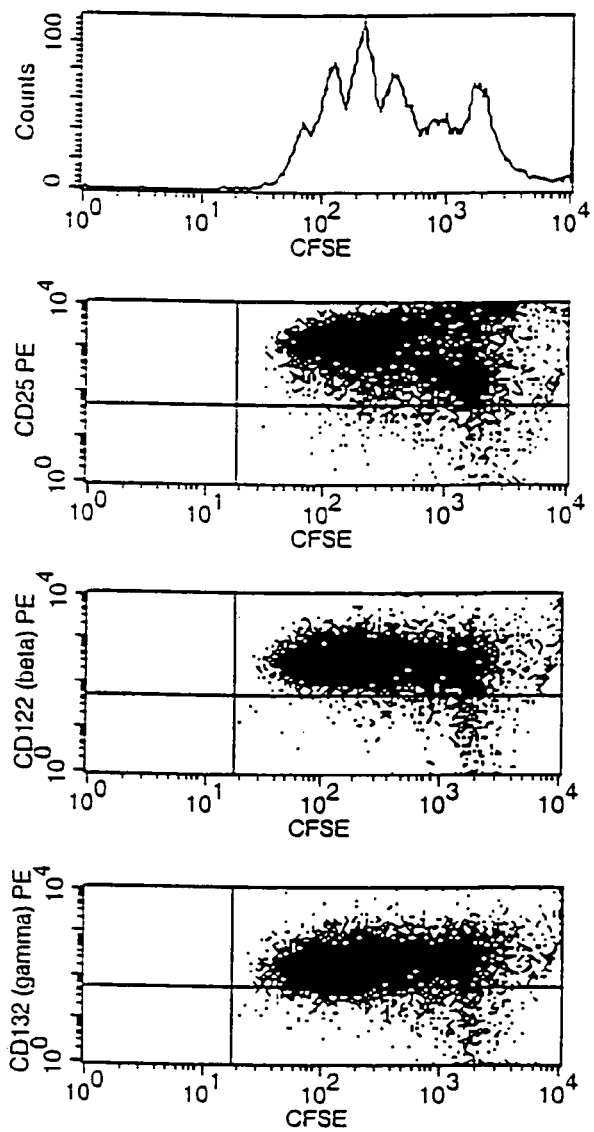
FIG. 3B is a series of plots depicting expression of IL-2 receptor α, β and γ chains by dividing T cells in vitro. CFSE-labeled cells lymphocytes were stimulated with anti-CD3 (2 μg/ml) in vitro for three days. Cell division and the expression of IL-2 receptor subunits were analyzed by fluorescence-activated cell sorting (FACS).
Figure 3C:
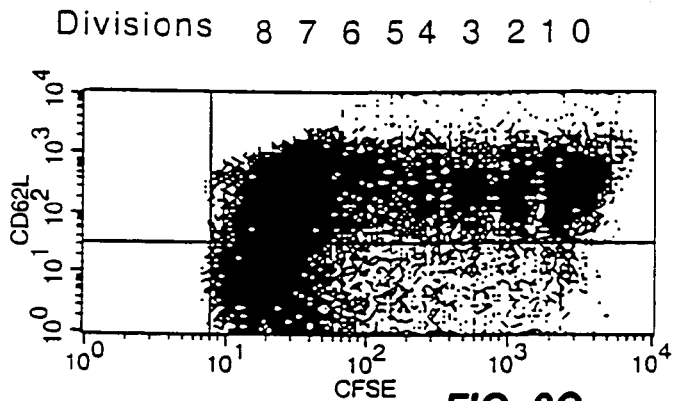
FIG. 3C is a plot depicting expression of L-selectin by dividing T cells in vivo. Cells were harvested from lymph nodes of host mice three days after intravenous injection of CFSE-labeled cells and stained with PE-anti-CD62L mAb. The quadrant was set based on cells stained with isotype control mAb.

Second, stimulation of CFSE-labeled T cells in vitro resulted in a uniform expression of all three subunits of the IL-2 receptor (FIG. 3B). This suggests that regulation of IL-2 receptor expression in vivo is distinct from that in vitro. The IL-2 receptor α chain is known to be sensitive to proteolytic cleavage in vivo in a manner that is similar to the selectins (Hemar et al., *J. Cell. Biol.* 129:55-64, 1995). Staining for L-selectin expression by dividing T cells in vivo showed that L-selectin was expressed at high levels during the first five cell divisions (FIG. 3C), suggesting that the failure to detect IL-2 receptor α chain expression during the first five cell divisions is not due to rapid proteolytic cleavage. To determine whether T cells in the first five cell divisions are capable of expressing the IL-2 receptor α chain, T cells at the second cell division, which did not express IL-2 receptor α chain, were sorted and stimulated in vitro with immobilized anti-CD3 and soluble anti-CD28 for three days. These sorted T cells continued to divide upon in vitro restimulation, and all dividing T cells expressed the IL-2 receptor α chain. Clearly, expression of IL-2 receptor α chain in vivo and in vitro is differentially regulated.

Figure 4A:
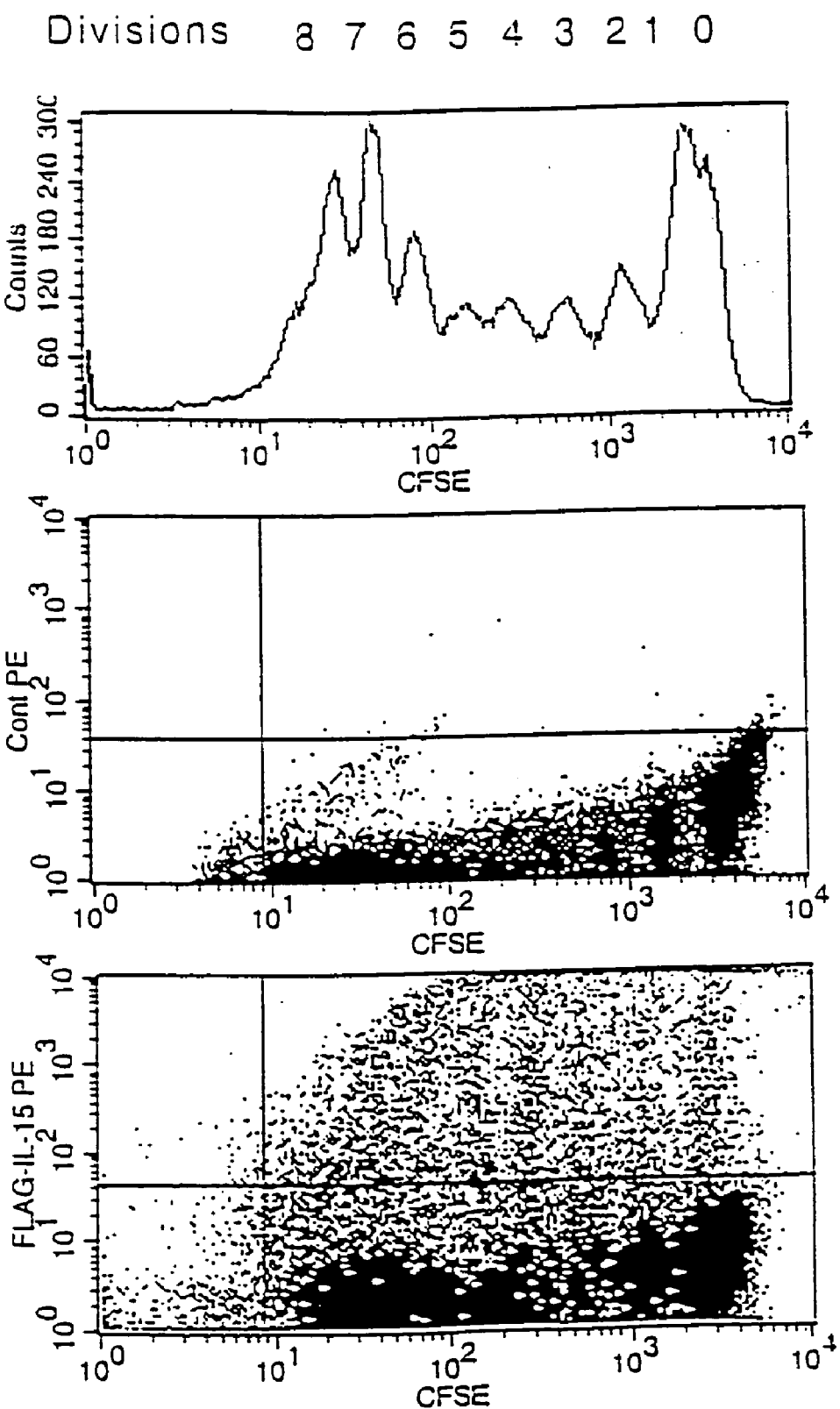
FIG. 4A is a series of plots depicting expression of IL-15 receptor α chain by dividing T cells in vivo three days after intravenous injection of CFSE-labeled cells. Cells were stained with an IL-15-FLAG fusion protein, followed by staining with biotinylated anti-FLAG mAb and PE-streptavidin. Cell staining in the absence of IL-15-FLAG was included as a control.

As the receptor for IL-15 also uses the IL-2 receptor β and γ chains as critical signaling components (Tagaya et al., *Immunity* 44:329-336, 1996), which are highly expressed during the first five cell divisions, we asked whether cells express an IL-15 receptor α chain that renders them responsive to IL-15 during initial cell divisions. Application of an IL-15-FLAG fusion protein as a primary staining reagent (Chae et al., *J. Immunol.* 157:2813-2819, 1996), demonstrated that the IL-15 receptor α chain is clearly detectable, albeit at low levels, on dividing T cells regardless the number of cell divisions (FIG. 4A). The α chain for IL-2 receptor was not detected on all dividing T cells in vivo. Thus, selective expression of the α chain for IL-15 receptor, but not for IL-2 receptor, along with the expression of shared β and γ chains during the first five cell divisions, suggests that initial cell division in vivo is likely IL-15- but not IL-2-dependent.

Figure 4B:
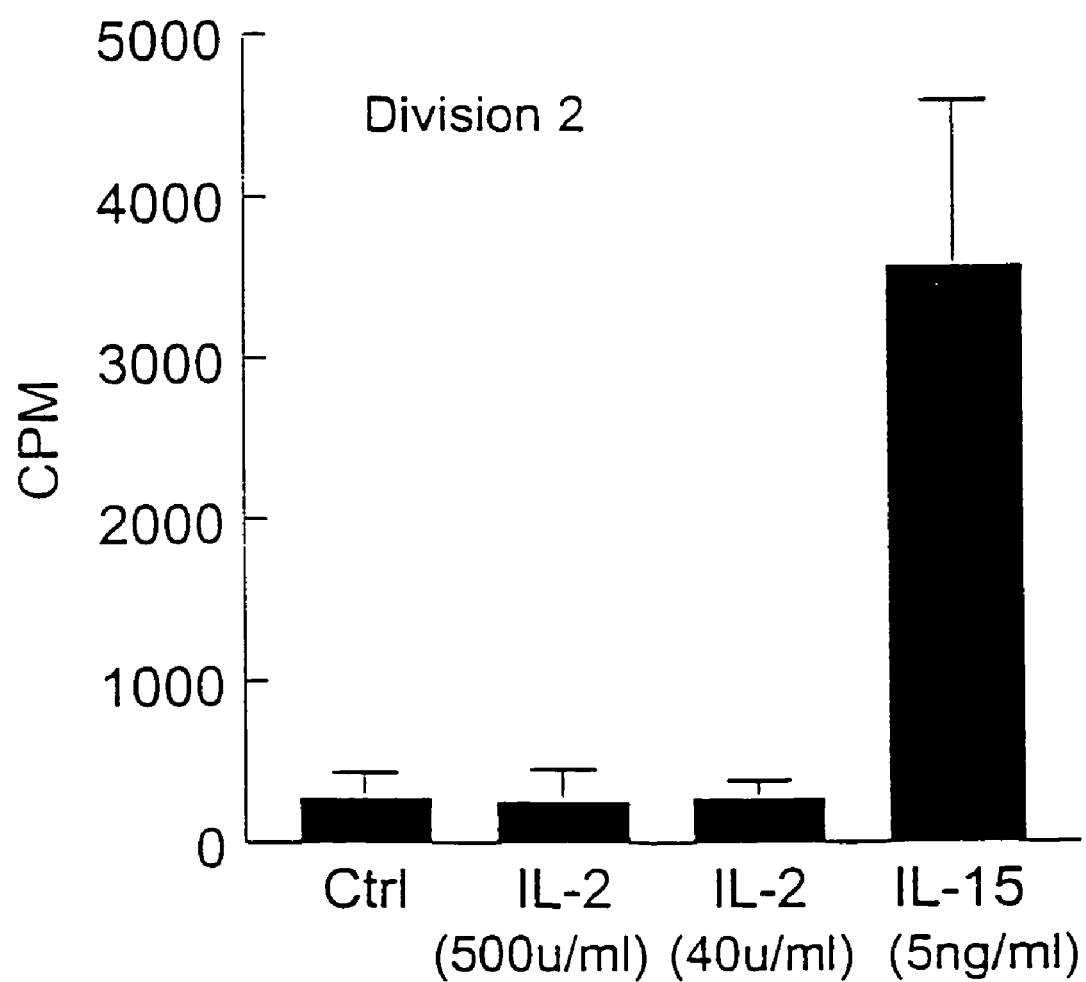
FIG. 4B is a bar graph depicting the different response of in vivo dividing T cells to IL-2 and IL-15 in vitro. CFSE-labeled lymphocytes were stimulated in vivo for three days and cell division was analyzed by examining the CFSE profile. T cells in the second cell division were sorted and cells ($1 \times 10^4$) were cultured in vitro with IL-2 or IL-15 for two days. Cellular proliferation was determined by $^3$H-TdR uptake. The results are presented as the mean CPM±SD of triplicate assays.

To test this hypothesis, IL-2 production was assessed in dividing T cells in vivo. Intracellular IL-2 staining revealed that IL-2 was highly expressed only by cells that have divided more than five times. Treatment of host mice with saturating doses of cytolytic anti-CD25 mAb failed to inhibit the first five cell divisions (relative to control Ab treated mice), and dividing cells in the first and fifth divisions were remarkably similar in anti-CD25 treated mice and in control mice. Furthermore, T cells at the second cell division in vivo were sorted and cultured in vitro in the presence of IL-2 or IL-15, and cell proliferation was analyzed by $^3$H-TdR uptake. IL-2, provided in doses as high as 500 µ/ml in culture, failed to support T cell proliferation. In contrast, IL-15 stimulated vigorous cell proliferation (FIG. 4B).

Figure 5A:
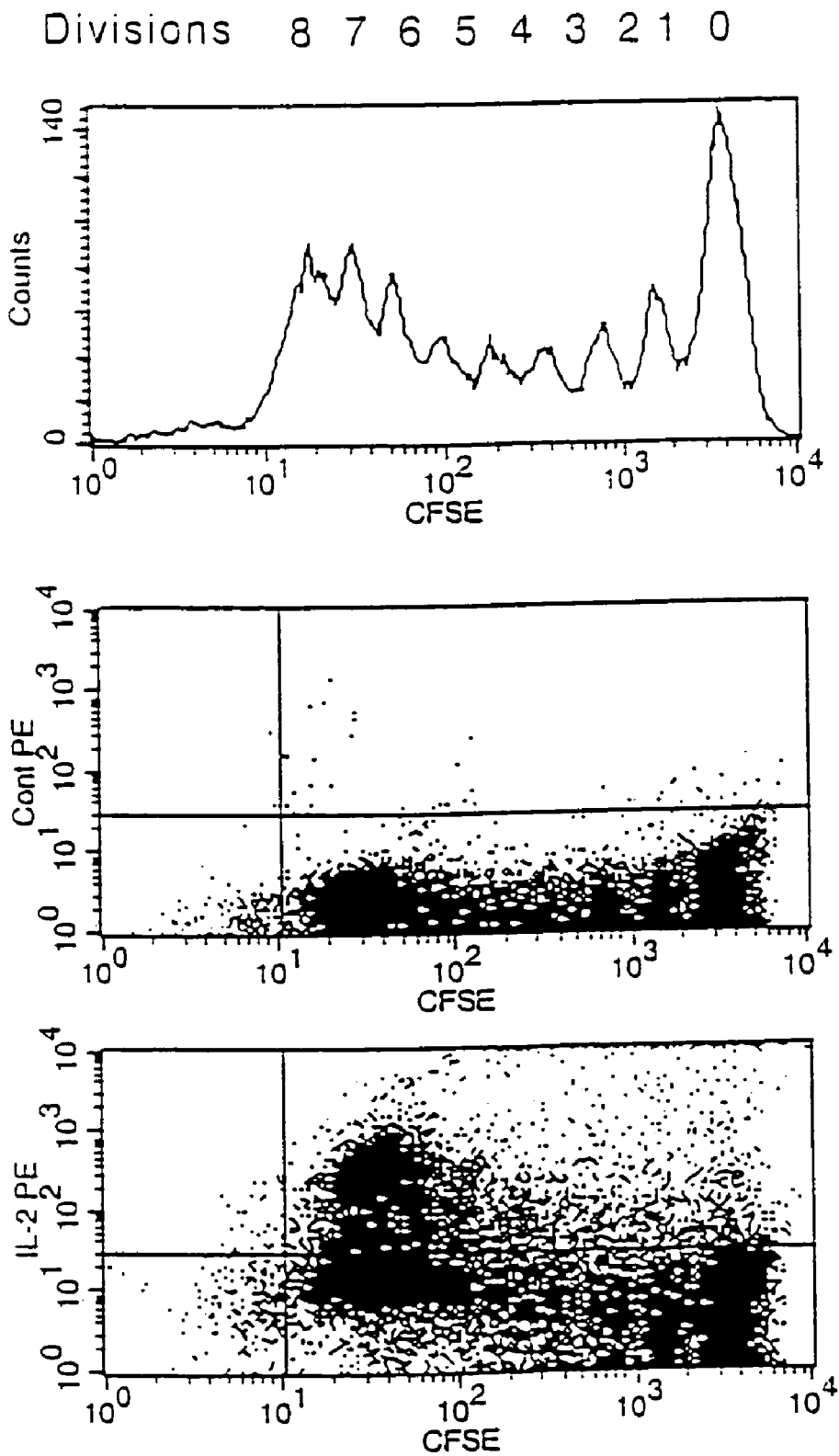
FIG. 5A is a series of plots depicting intracellular IL-2 staining of in vivo dividing T cells. CFSE-labeled cells were stimulated in vivo for three days. Cells harvested from the host spleen were stimulated in vitro with PMA and ionomycin for four hours in the presence of GolgiStop™. Cells were then fixed, permeablized, and stained for IL-2 production. Cells stained with isotype control mAb were included as a control.
Figure 5C:
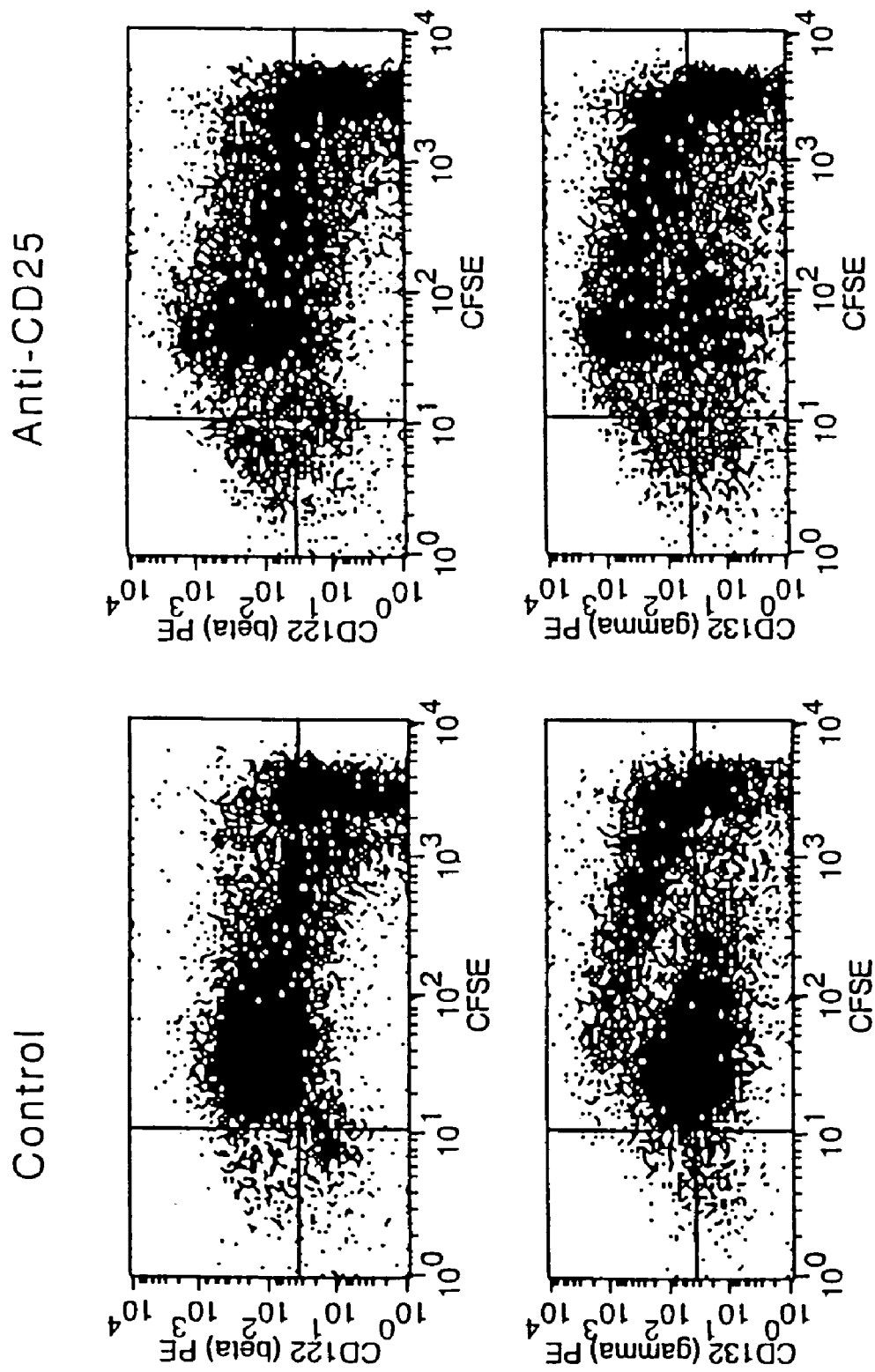
FIG. 5C is a series of plots depicting the effect of anti-CD25 treatment on γc expression by dividing T cells in vivo. Host mice were given anti-CD25 mAb at 1 mg/day (i.p.) for three days immediately before intravenous injection of CFSE-labeled cells. Expression of IL-2 receptor β and γ chains on dividing T cells in vivo was determined on day three (i.e., three days after injection of CFSE-labeled cells). Mice treated with an isotype control mAb (rat IgG1) were included as a control.
Figure 5D:
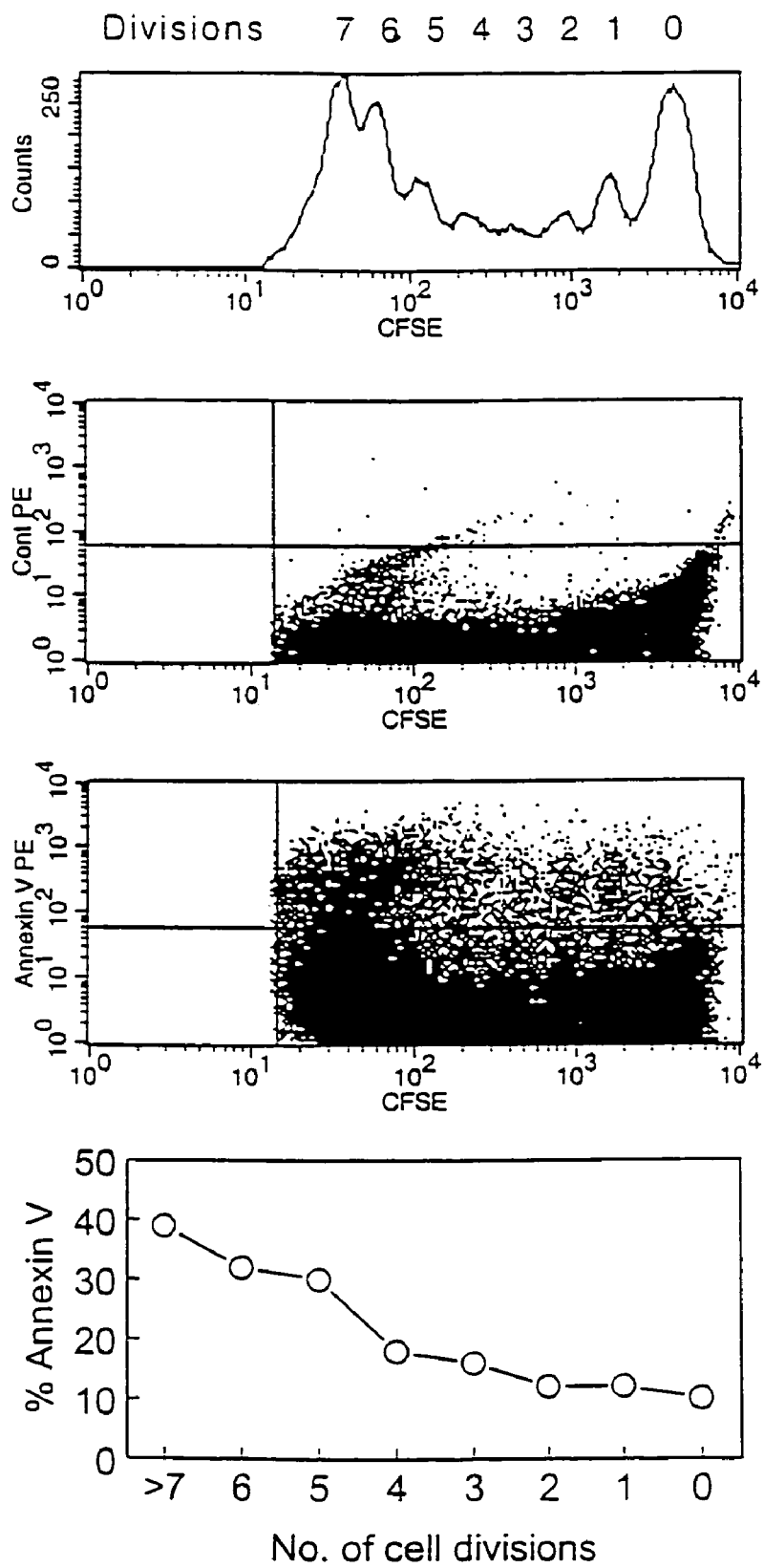
FIG. 5D is a series of plots depicting apoptotic cell death of in vivo dividing T cells. CFSE-labeled cells were stimulated in vivo for three days. Cells were harvested from the host spleen and stained with PE-annexin V. Cell division and apoptic cell death were analyzed by FACS.

The pattern of IL-2 expression in vivo is closely associated with upregulation of the IL-2 receptor α and β chains, and with markedly decreased expression of the common γ chain (FIG. 5A). This suggests that IL-2 regulates γ chain expression in vivo. To test this possibility, γ chain expression was examined in T cells from IL-2 deficient mice and wild type control mice. CD4$^+$ T cells from IL-2 deficient mice expressed very high levels of γ chain on the cell surface as compared to wild type controls (FIG. 5B). Treatment of host mice with anti-CD25 inhibited γ chain down regulation on dividing T cells in vivo, but this treatment had no effect on IL-2 receptor β chain expression (FIG. 5C).

Figure 5E:
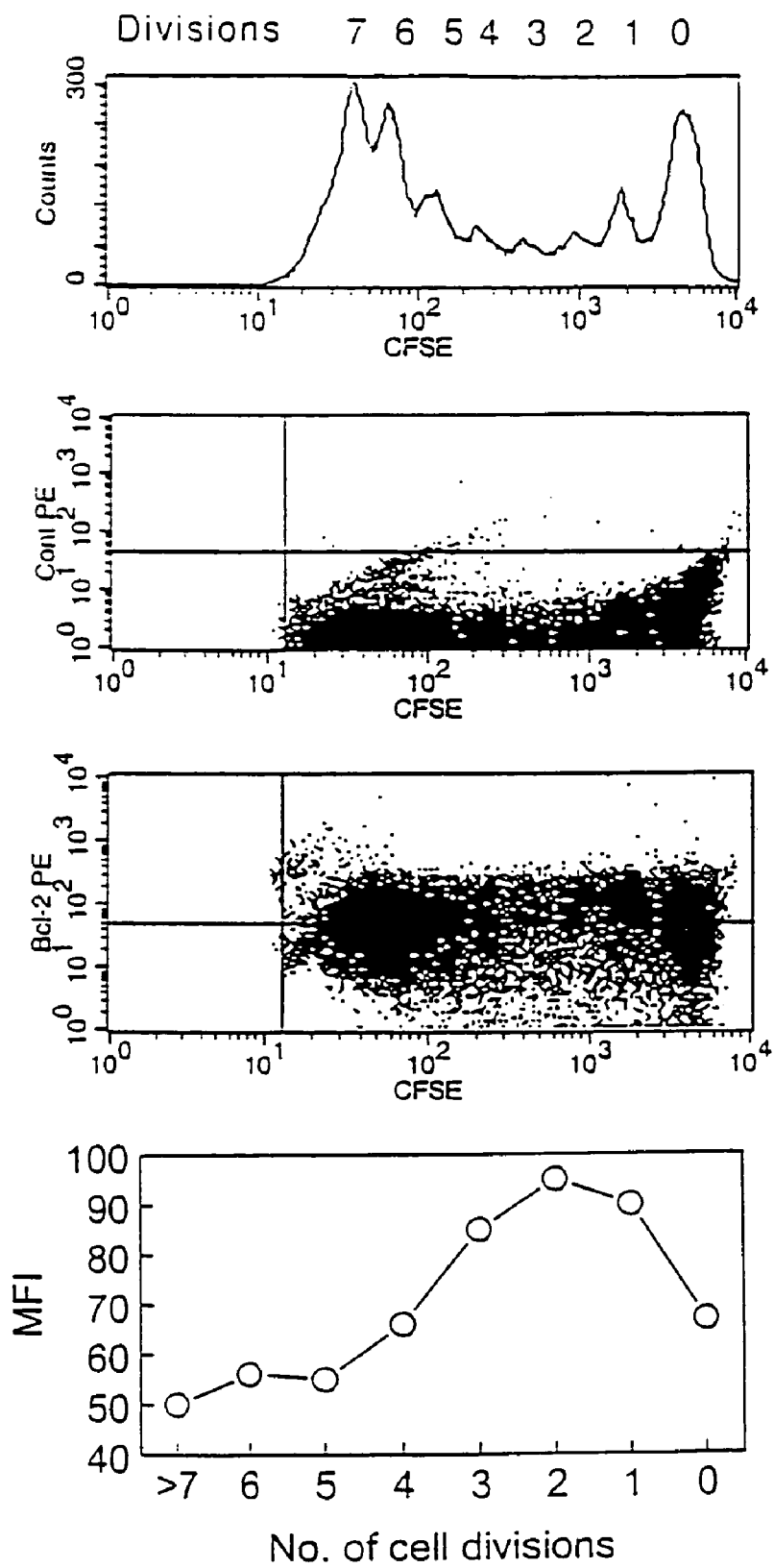
FIG. 5E is a series of plots depicting intracellular Bcl-2 expression by dividing T cells in vivo. CFSE-labeled cells were stimulated in vivo for three days. Cells harvested from the host spleen were stained with PE-anti-mouse Bcl-2 mAb or an isotype control mAb. Cell division and expression of Bcl-2 were analyzed by FACS.

The γ chain is a critical signaling element for all known T cell growth factors and γ chain signals are essential for cell survival, which is accomplished at least in part via sustained expression of Bcl-2 family anti-apoptotic proteins (Nakajima et al., *J. Exp. Med.* 185:189-195, 1997). To determine whether decreased γ chain expression after five cell divisions in vivo regulates clonal expansion, CFSE-labeled cells were stained with PE-annexin V after recovery from the hosts and apoptotic cell death of dividing T cells was analyzed in vivo. Precipitous cell death occurred after four cell divisions. Undivided cells (0 division) had <10% annexin V positive cells. After the sixth cell division, however, ~40% of the cells were annexin V positive. This type of cell death is not Fas dependent, as T cells from Fas mutant MRL-lpr mice had similar pattern of apoptotic cell death in vivo (Li et al., *J. Immunol.* 163:2500-2507, 1999). Staining for Bcl-2 expression showed that the mean channel fluorescence intensity of Bcl-2 staining was markedly decreased after four cell divisions (FIG. 5E). Thus, the signaling events upon γ chain down-regulation may fail to support sustained Bcl-2 expression and cells become susceptible to apoptotic cell death (Nakajima et al., *J. Exp. Med.* 185:189-195, 1997).

These results suggest that blocking IL-2 or IL-15 signaling will have different effects on T cell expansion in vivo. To explore this possibility further, CFSE-labeled lymphocytes from IL-2 deficient mice (H-2b) were injected into irradiated DBA/2 hosts (H-2d), cell division was analyzed in vivo three days later and compared with that in wild type control mice. T cells from IL-2 deficient mice continued to divide and expand in vivo. About 30% of CFSE-labeled cells entered the cell cycle, and the majority of the cells divided more than five times, compared to control.

Treating host mice with an IL-15 mutant /Fc, which acts as an IL-15 receptor specific antagonist (Kim et al., *J. Immunol.* 161:5742-5748, 1998), markedly reduced the proliferation frequency of CFSE-labeled T cells, and an overwhelming majority of CFSE-labeled cells failed to enter the cell cycle in the treated mice. Furthermore, treatment of host mice with blocking mAbs against the common γ chain, a shared signaling component of IL-2 and IL-15 receptors, also markedly inhibited T cell division in vivo. Thus, IL-2 and IL-15 regulate distinct aspects of T cell expansion in vivo, and administration of antagonists for these interleukins can suppress the immune response, as discussed above.

These results also demonstrate that γ chain downregulation requires T cell activation and cell cycle progression as well as IL-2 signaling. Clearly, γ chain downregulation in vivo is closely associated with IL-2 production and high affinity IL-2 receptor expression. In the absence of IL-2, γ chain is expressed at extremely high levels and blockade of IL-2 receptor inhibits γ chain downregulation in vivo on cycling T cells. Thus, these studies provide novel evidence that IL-2 and IL-15 regulate distinct aspects of primary T cell activation in vivo. Contrary to traditional beliefs and conclusions based on in vitro studies, IL-15 is a critical growth factor in initiating T cell division in vivo and IL-2's unique role in vivo is to control the magnitude of clonal expansion by regulating γ chain expression on cycling T cells.

These results support the clinical applications described above. Attempts to boost T cell response with exogenous IL-2 in tumor immunity and AIDS may promote premature T cell death and therapies to block IL-2 in tolerance induction and autoimmunity may induce unwanted T cell expansion. Furthermore, staged and combined targeting of IL-15 and IL-2 represent an important way to block T cell activation in T cell dependent cytopathic conditions.

Lytic IL-2/Fc Lyses IL-2R-Bearing Cells and Binds to FcRI

Figure 6:
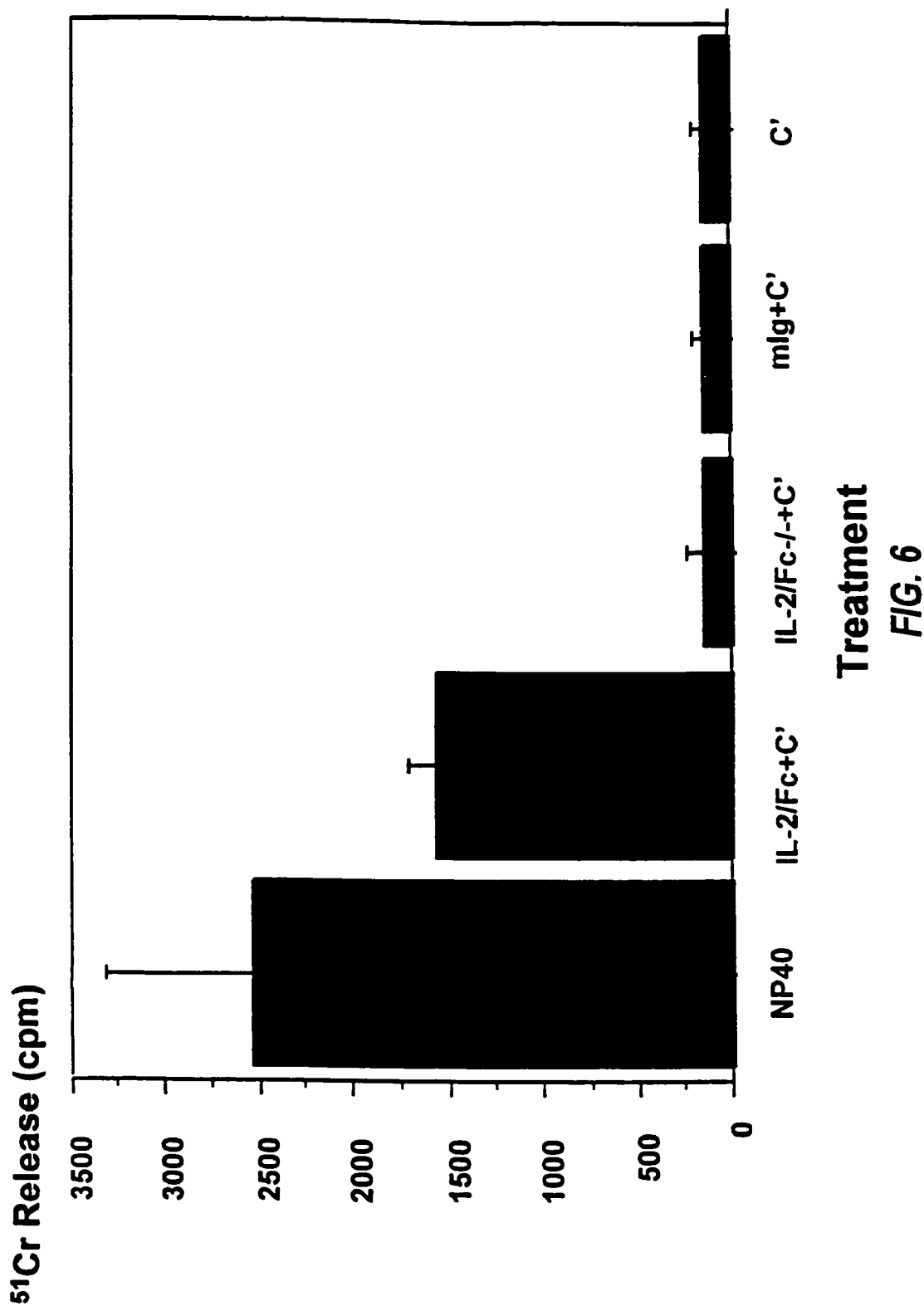
FIG. 6 is a bar graph depicting the results of an experiment in which cell death (assessed by release of the isotope $^{51}$Cr from CTLL-2 cells; see the x axis) was assessed following treatment with various agents. NP40 is a detergent; IL-2/Fc is a fusion protein that contains IL-2 and the Fc region of an IgG molecule (this molecule is lytic); C' is rat complement; IL-2/FC−/− is a non-lytic IL-2-containing fusion protein; and mIg is a murine immunoglobulin. This study supports the conclusion that cytolytic IL-2/Fc lyses IL-2R-bearing CTLL-2 cells, but non-lytic IL-2/Fc does not.

Cells of a T cell line (CTLL-2 cells; $10^6$) were labeled with 100 mCi $^{51}$Cr and incubated with a lytic form of IL-2/Fc and rat low-toxic complement (C'), a non-lytic form of IL-2/Fc and C', murine immunoglobulin and C' (a negative control) or C' alone (a negative control at 0.5 μg/ml). Another group of the same cells was treated with a detergent (1% NP40) (a positive control). Cell lysis was measured by $^{51}$Cr release. The degree of lysis observed in the presence of the detergent represents 100% lysis. Specific lysis following treatment as described above was calculated according to the formula: % specific lysis=[(experimental cpm−background cpm)/(total release cpm−background cpm)×100%]. The results, which are shown in FIG. 6, support the conclusion that cytolytic IL-2/Fc lyses IL-2R-bearing CTLL-2 cells, but non-lytic IL-2/Fc does not.

Figure 7:
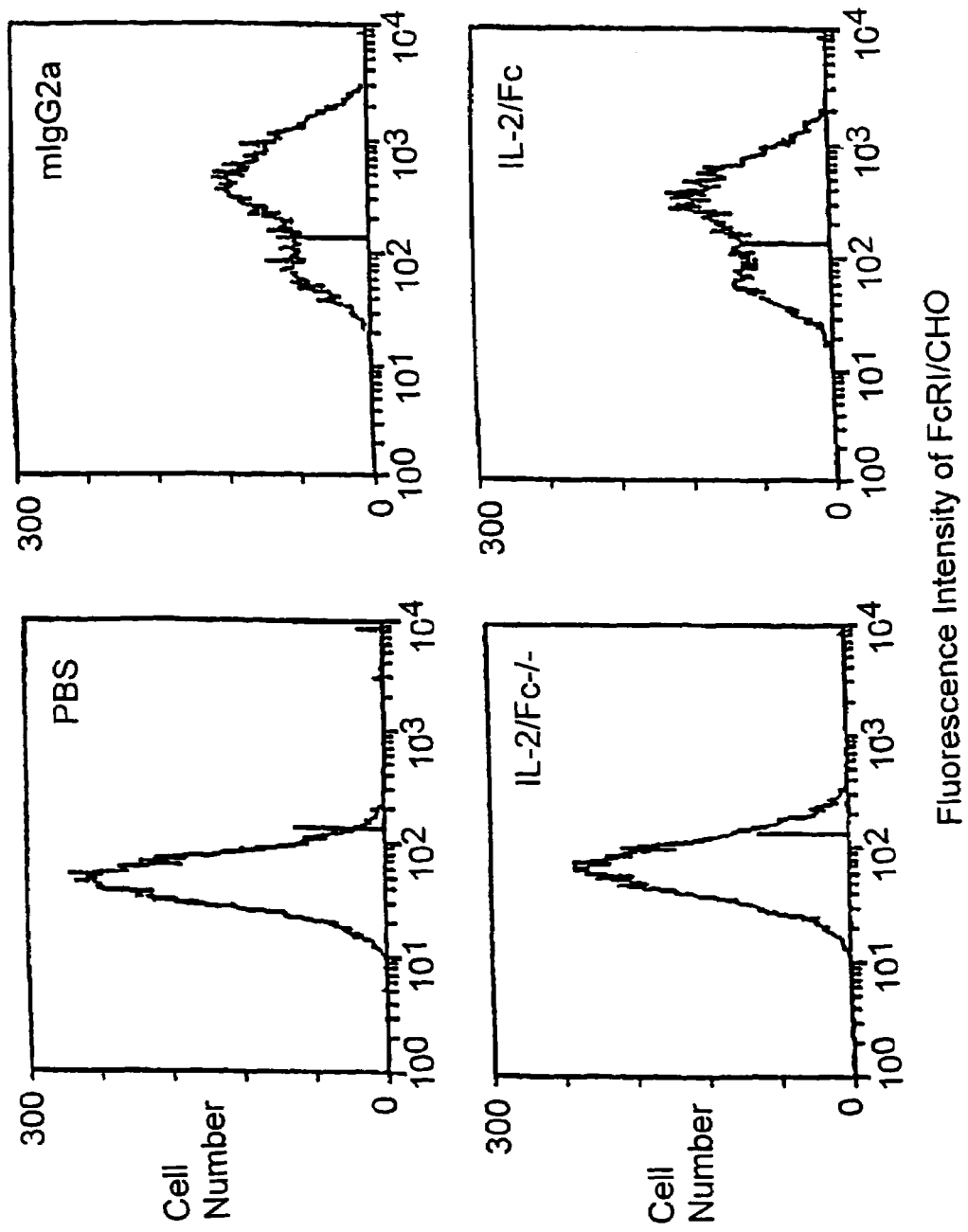
FIG. 7 is a series of histographs. The fluorescence intensity of FcRI on CHO (Chinese hamster ovary) cells was measured after the cells were exposed to phosphate buffered saline (PBS; upper left), a murine immunoglobulin (mIgG2a; upper right), a non-lytic IL-2/Fc molecule (IL-2/Fc−/−; lower left), and a lytic IL-2 containing fusion protein (IL-2/Fc; lower right). In each histogram, cell number is plotted against the fluorescence intensity of FcRI/CHO. This study supports the conclusion that cytolytic IL-2/Fc binds to FcRI, but non-lytic IL-2/Fc does not.

To assess the ability of lytic and nonlytic IL-2/Fc to bind Fc receptors on FcRI-transfected CHO cells (murine FcRI, FcRII, and IL-2R-negative), FcRI transfectants were preincubated with PBS, mIgG2a, lytic IL-2/Fc, or nonlytic IL-2/Fc. After washing, fluorescent-conjugated goat anti-mouse Fc was used to stain the cells for FACS analysis. As shown in FIG. 7, cytolytic IL-2/Fc can bind FcRI, but lytic IL-2/Fc cannot.

Lytic IL-2/Fc is Effective in Preventing Diabetes in an Adoptive Transfer Model

Figure 13:
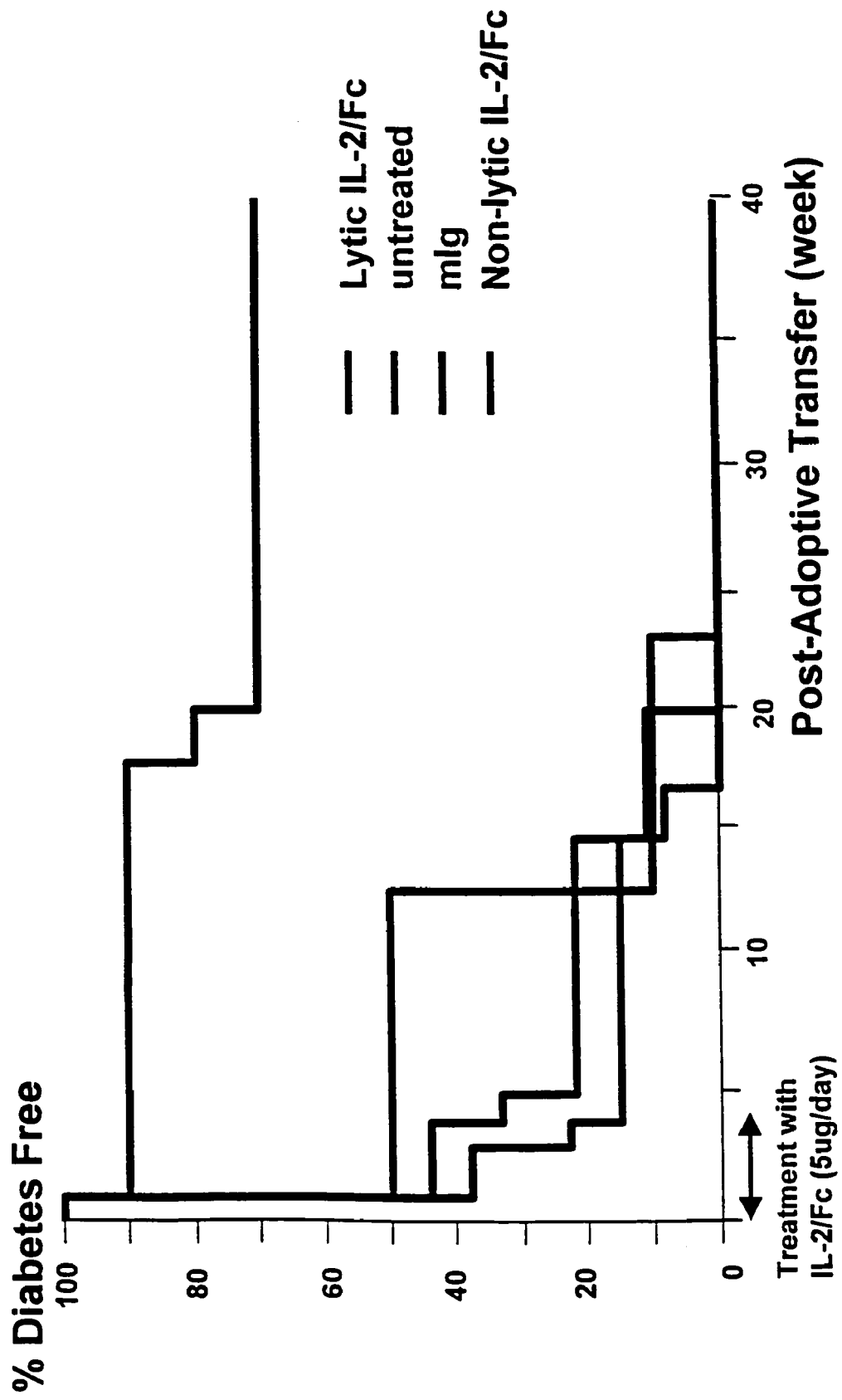
FIG. 13 is a line graph that plots the % of animals that remained diabetes free over time following treatment with a lytic IL-2/Fc molecule, a murine immunoglobulin (mIg), and a non-lytic IL-2/Fc molecule. Cytolytic IL-2/Fc blocked autoimmunity, but lytic IL-2/Fc did not.

Two different variants of IL-2/Fc were created. The first contained an Fc terminus derived from murine IgG2a that will mediate CDC and CDCC (IL-2/Fc), and the second was a point mutated Fc portion that would not activate CDC or CDCC (IL-2/Fc−/−). Whereas IL-2/Fc mediates CDC in IL-2R bearing cells (such as those of the murine CTLL-2 T cell line) and binds to FcRI, IL-2/Fc−/− does not (FIGS. 6 and 7$_{[TM1]}$). Moreover, the lytic IL-2/Fc molecule will prevent the development of diabetes in an NOD adoptive transfer model, but a non-lytic form of the moleucle (IL-2/Fc−/−) is uneffective (FIG. 13). In the animal model, monodispersed spleen cells were depleted of erythrocytes by treatment with ACK Lysing Buffer (BioWhittaker Inc., Walkersville, Md.). Eight to 12 week-old irradiated (700-rad) NOD male recipients, which were non-diabetic, were then injected with $2\times10^7$ splenic leukocytes from acutely diabetic female NOD mice (hyperglycemia<two weeks). Blood glucose levels (BGL) were tested weekly, and diabetes was diagnosed when the BGL was greater than 16.5 mmol/L on any single measurement or greater than 13.8 mmol/L on 3 consecutive days. As shown in FIG. 13, most of the animals remained diabetes free even after the treatment was discontinued.

As noted above, the assays and animal models presented herein can be used to test various combinations of the agents of the invention for therapeutic efficacy.

Figure 8:
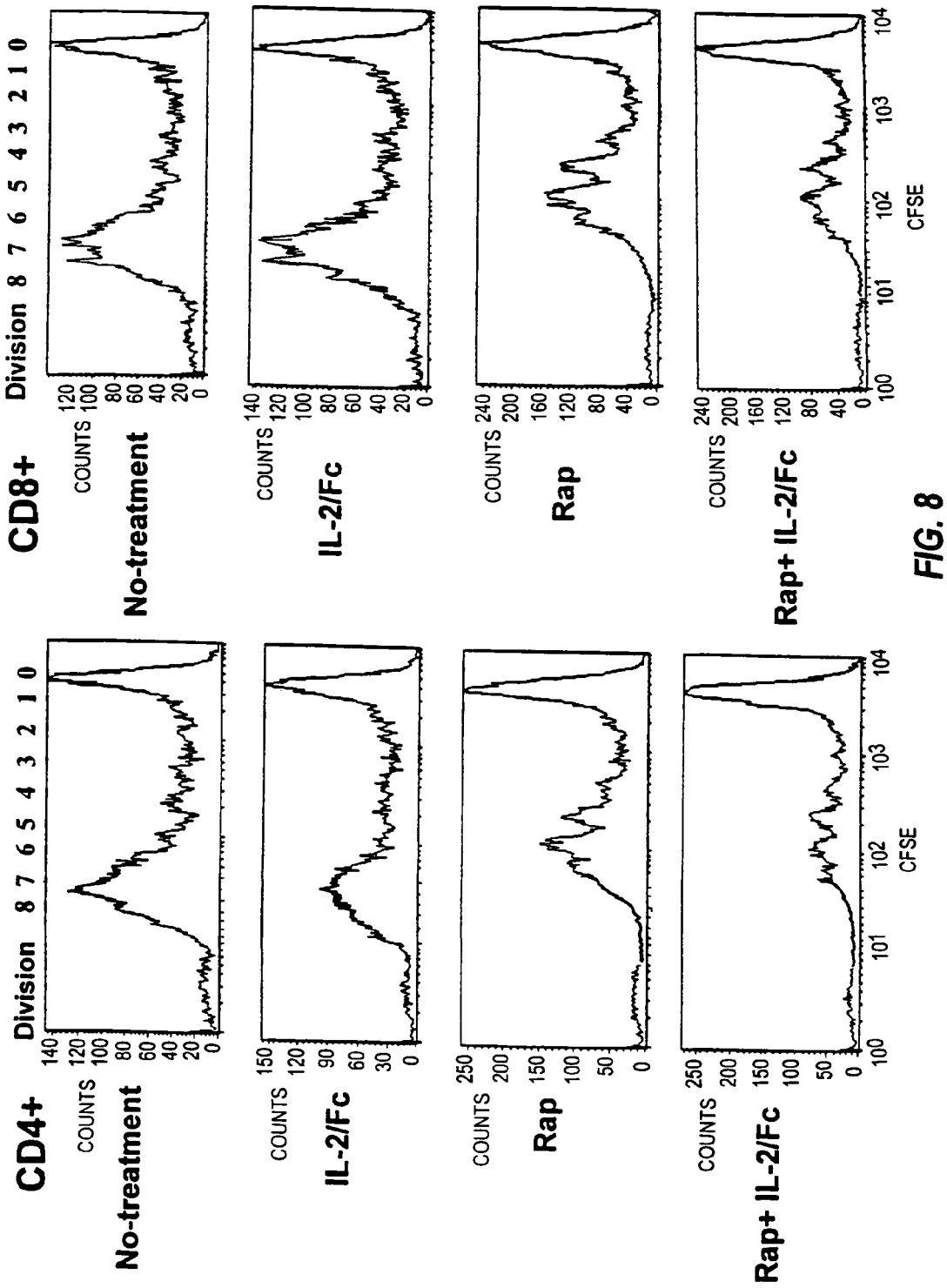
FIG. 8 is a series of eight plots depicting the proliferative response of CD4$^+$ (left-hand side) and CD8$^+$ (right-hand side) T cells in vivo. The cells were labeled with CFSE and stimulated in vivo for three days with a lytic molecule (IL-2/Fc), a cell proliferation agent (rapamycin (Rap)), or the two agents combined. As a negative control, one group of animals was not treated. IL-2/FC was analyzed by their CFSE profile. This study supports the conclusion that rapamycin inhibits IL-2 proliferative signaling.
Figure 9:
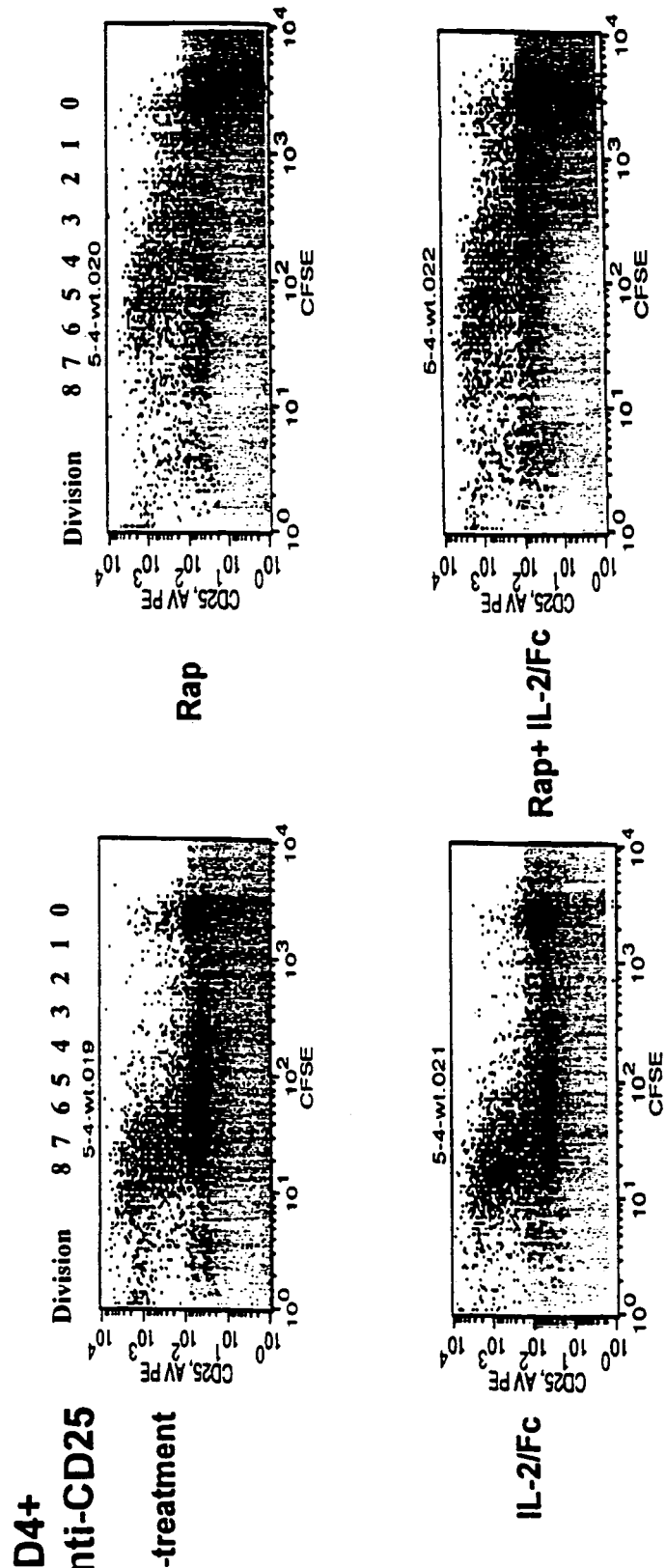
FIG. 9 is a series of four plots obtained from an experiment in which CFSE-labeled lymphocytes were stimulated in vivo for three days. The expression of an IL-2R α chain on dividing T cells was assessed by FACS in animals that received no treatment (upper left), rapamycin alone (Rap; upper right), IL-2/Fc alone (lower left), or a combination of rapamycin and IL-2/Fc (Rap+IL-2/Fc; lower right). This study supports the conclusion that treatment with rapamycin and IL-2/Fc promotes expression of the a subunit of the IL-2R during early T cell proliferation in vivo.
Figure 10:
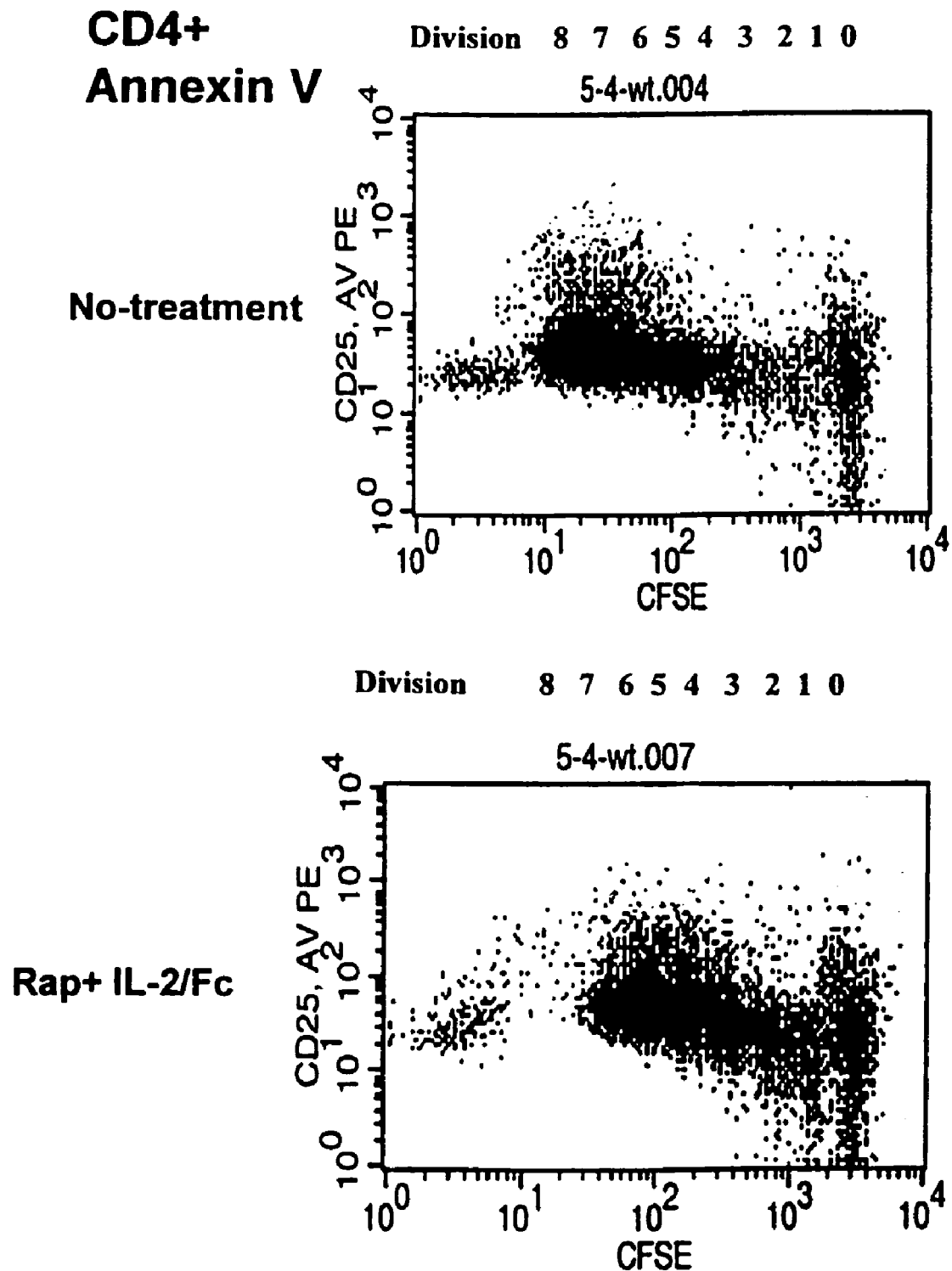
FIG. 10 is a pair of plots obtained when CFSE-labeled lymphocytes were stimulated in vivo for three days and analyzed by FACS. The expression of Annexin V on dividing T cells (CD4$^+$) was assessed in animals that received no treatment (left hand panel) or rapamycin and IL-2/Fc (Rap+IL-2/Fc; right hand panel). This study supports the conclusion that rapamycin and IL-2/Fc treatment promotes apoptosis of CD4+ cells during early T cell proliferation in vivo.

Rapamycin Inhibits T Cell Proliferation in an in Vivo Graft Versus Host Model, but Does Not Inhibit Apoptosis of Activated T Cells In an in vivo graft versus host model (as described above), the fate of host reactive T cells in the presence of IL-2/Fc and rapamycin was analyzed. As shown in FIG. 8, rapamycin will inhibit the proliferation of CD4$^+$ and CD8$^+$ T cells, even in the presence of IL-2/Fc, but will allow the expression of a functional IL-2R. As evidenced by Annexin V staining, antigen activated host reactive T cells will undergo apoptosis in the presence of IL-2/Fc and rapamycin (FIG. 10).

The Compositions of the Invention Permit Long-Term Survival of Islet and Skin Allografts To prevent rejection of either allogeneic islets transplanted into acutely diabetic NOD recipients or rejection of skin grafts transplanted onto NOD mice, a combination of agents promoting T cell death and inhibiting T cell proliferation was used. As shown in FIGS. 11 and 12, a combination of lytic IL-2/Fc, mutIL-15/Fc and rapamycin proved effective in preventing graft rejection (and more effective than other treatment regimens tested). Graft survival and graft function persisted throughout the observation period shown, and most grafts survived after discontinuation of the therapy. This dramatic effect is believed to be due to the combination of agents used (agents that promote T cell death as well as inhibit T cell proliferation).

A number of embodiments of the invention have been described. Nevertheless, it will be understood that various modifications may be made without departing from the spirit and scope of the invention. Accordingly, other embodiments are within the scope of the following claims.

What is claimed is:

1. A therapeutic composition comprising a first agent that targets an interleukin-15 receptor (IL-15R), a second agent that targets an interleukin-2 receptor (IL-2R), and rapamycin, wherein the first agent comprises a mutant IL-15 polypeptide that has a substitution of aspartate for glutamine at positions 149 and 156 of SEQ ID NO:4, the mutant IL-15 polypeptide being optionally fused to the Fc region of an immunoglobulin, and the second agent comprises an IL-2 polypeptide that binds an IL-2R, wherein the IL-2 polypeptide is fused to the Fc region of an immunoglobulin.

2. The therapeutic composition of claim 1, wherein the mutant IL-15 polypeptide binds an IL-15Rα subunit of an IL-15R.

3. The therapeutic composition of claim 1, wherein the immunoglobulin is an immunoglobulin of the G class (an IgG).

4. The therapeutic composition of claim 1, wherein the mutant IL-15 polypeptide is at least 95% identical to wild-type IL-15.

5. The therapeutic composition of claim 1, wherein the Fc region of an immunoglobulin, when present and fused to the mutant IL-15 polypeptide or the IL-2 polypeptide, is a target-cell depleting Fc region.

6. A therapeutic composition comprising a first agent that targets an interleukin-15 receptor (IL-15R), a second agent that targets an interleukin-2 receptor (IL-2R) and rapamycin, wherein the first agent consists of a mutant IL-15 polypeptide that is fused to the Fc region of an immunoglobulin, wherein the mutant IL-15 polypeptide has a substitution of aspartate for glutamine at positions 149 and 156 of SEQ ID NO:4, and the second agent consists of an IL-2 polypeptide that binds an IL-2R and is fused to the Fc region of an immunoglobulin.

7. The therapeutic composition of claim 6, wherein the mutant IL-15 polypeptide binds an IL-15Rα subunit of an IL-15R.

8. The therapeutic composition of claim 6, wherein the immunoglobulin is an immunoglobulin of the G class (an IgG).

9. The therapeutic composition of claim 6, wherein the mutant IL-15 polypeptide is at least 95% identical to wild-type IL-15.

10. The therapeutic composition of claim 6, wherein the Fc region fused to the mutant IL-15 polypeptide or the Fc region fused to the IL-2 polypeptide, is a target-cell depleting Fc region.

* * * * *

UNITED STATES PATENT AND TRADEMARK OFFICE
CERTIFICATE OF CORRECTION

PATENT NO. : 7,579,439 B2 Page 1 of 1
APPLICATION NO. : 10/749699
DATED : August 25, 2009
INVENTOR(S) : Xian Chang Li, Terry B. Strom and Xin Xiao Zheng It is certified that error appears in the above-identified patent and that said Letters Patent is hereby corrected as shown below:

Title Page, col. 1, Item [56] (Other Publications), line 1, delete "Immunlogy," and insert -- immunology, --.

Title Page, col. 1, Item [56] (Other Publications), line 3, delete "Transplantaion" and insert -- Transplantation --.

Title Page, col. 2, Item [56] (Other Publications), line 10, delete "270(5)" and insert -- 270(50) --.

Title Page, col. 2, Item [56] (Other Publications), line 18, delete "LymphocytesArthritis" and insert -- Lymphocytes. Arthritis --.

Title Page, col. 2, Item [56] (Other Publications), line 27, delete "cytoxin" and insert -- cytotoxin --.

Signed and Sealed this

Twelfth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,579,439 B2 | Page 1 of 1 |
| APPLICATION NO. | : 10/749699 | |
| DATED | : August 25, 2009 | |
| INVENTOR(S) | : Terry B. Strom | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 318 days.

Signed and Sealed this

Second Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,579,439 B2 | Page 1 of 1 |
| APPLICATION NO. | : 10/749699 | |
| DATED | : August 25, 2009 | |
| INVENTOR(S) | : Terry B. Strom | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 319 days.

Signed and Sealed this

Seventh Day of December, 2010

David J. Kappos
*Director of the United States Patent and Trademark Office*